United States Patent
Looney et al.

(10) Patent No.: US 7,279,177 B2
(45) Date of Patent: Oct. 9, 2007

(54) HEMOSTATIC WOUND DRESSINGS AND METHODS OF MAKING SAME

(75) Inventors: Dwayne Lee Looney, Flemington, NJ (US); Jian Xin Guo, Bridgewater, NJ (US); Guanghui Zhang, Belle Mead, NJ (US); Sanyog Manohar Pendharkar, Old Bridge, NJ (US); Anne Jessica Gorman, Hightstown, NJ (US); Thomas Lee Craven, Bridgewater, NJ (US); Michelle Bermel, Willow Grove, PA (US)

(73) Assignee: Ethicon, Inc., Somerville, NJ (US)

( * ) Notice: Subject to any disclaimer, the term of this patent is extended or adjusted under 35 U.S.C. 154(b) by 514 days.

(21) Appl. No.: 10/396,226

(22) Filed: Mar. 25, 2003

(65) Prior Publication Data

US 2004/0005350 A1 Jan. 8, 2004

Related U.S. Application Data

(63) Continuation-in-part of application No. 10/186,021, filed on Jun. 28, 2002, and a continuation-in-part of application No. 10/304,781, filed on Nov. 26, 2002, now abandoned, and a continuation-in-part of application No. 10/305,040, filed on Nov. 26, 2002, now abandoned, and a continuation-in-part of application No. 10/304,472, filed on Nov. 26, 2002, now abandoned, and a continuation-in-part of application No. 10/326,244, filed on Dec. 20, 2002.

(51) Int. Cl.
 *A61F 13/00* (2006.01)
 *A61L 15/00* (2006.01)

(52) U.S. Cl. ...................... 424/443; 424/445; 424/446; 424/447

(58) Field of Classification Search ................ 424/443, 424/484–489
See application file for complete search history.

(56) References Cited

U.S. PATENT DOCUMENTS

| 2,517,772 A | 8/1950 | Doub et al. |
| 2,773,000 A | 12/1956 | Masci et al. |

(Continued)

FOREIGN PATENT DOCUMENTS

| CS | 217243 B | 12/1982 |

(Continued)

OTHER PUBLICATIONS

European Search Report dated Sep. 20, 2004, for corresponding EP application 04253808.2.

(Continued)

*Primary Examiner*—Isis Ghali

(57) ABSTRACT

The present invention is directed to a hemostatic wound dressing that utilizes a fibrous, fabric substrate made from carboxylic-oxidized cellulose and containing a first surface and a second surface opposing the first surface, the fabric having flexibility, strength and porosity effective for use as a hemostat; and further having a porous, polymeric matrix substantially homogeneously distributed on the first and second surfaces and through the fabric, the porous, polymeric matrix being made of a biocompatible, water-soluble or water-swellable cellulose polymer, wherein prior to distribution of the polymeric matrix on and through the fabric, the fabric contains about 3 percent by weight or more of water-soluble oligosaccharides.

14 Claims, 20 Drawing Sheets

U.S. PATENT DOCUMENTS

| | | | |
|---|---|---|---|
| 2,914,444 | A | 11/1959 | Smith |
| 3,328,259 | A | 6/1967 | Anderson |
| 3,328,529 | A | 6/1967 | Anderson |
| 3,364,200 | A | 1/1968 | Aston et al. |
| 3,868,955 | A | 3/1975 | Siragusa et al. |
| 4,289,824 | A | 9/1981 | Smith |
| 4,407,787 | A | 10/1983 | Stemberger |
| 4,600,574 | A | 7/1986 | Lindner |
| 4,626,253 | A | 12/1986 | Broadnax, Jr. |
| 4,752,466 | A | 6/1988 | Saferstein et al. |
| 4,840,626 | A | 6/1989 | Linksy |
| 5,134,229 | A | 7/1992 | Saferstein et al. |
| 5,180,398 | A | 1/1993 | Boardman et al. |
| 5,409,703 | A | 4/1995 | Hall |
| 5,643,596 | A | 7/1997 | Pruss et al. |
| 5,645,849 | A | 7/1997 | Pruss et al. |
| 5,821,343 | A | 10/1998 | Keogh |
| 5,866,165 | A | 2/1999 | Liu et al. |
| 5,914,118 | A | 6/1999 | Yamamura et al. |
| 5,925,552 | A | 7/1999 | Keogh et al. |
| 5,945,319 | A | 8/1999 | Keogh |
| 6,017,741 | A | 1/2000 | Keogh |
| 6,214,808 | B1 | 4/2001 | Soe et al. |
| 6,261,679 | B1 | 7/2001 | Chen et al. |
| 6,306,424 | B1 | 10/2001 | Vyakarnam et al. |
| 6,333,029 | B1 | 12/2001 | Vyakarnam et al. |
| 6,365,149 | B2 | 4/2002 | Vyakarnam et al. |
| 6,500,777 | B1 | 12/2002 | Wiseman et al. |
| 2001/0025154 | A1 | 9/2001 | Rapp |
| 2002/0012693 | A1 | 1/2002 | Cohen et al. |
| 2002/0120348 | A1 | 8/2002 | Melican et al. |
| 2003/0073663 | A1 | 4/2003 | Wiseman et al. |

FOREIGN PATENT DOCUMENTS

| | | | |
|---|---|---|---|
| CS | 235108 | B1 | 5/1985 |
| CS | 238016 | B1 | 11/1985 |
| EP | 0 177 064 | A | 4/1986 |
| EP | 0 216 378 | A2 | 4/1987 |
| EP | 0 372 969 | A | 6/1990 |
| EP | 0468114 | A2 | 1/1992 |
| EP | 0 636 378 | A | 2/1995 |
| EP | 0 815 879 | A2 | 6/1997 |
| EP | 1172115 | A1 | 1/2002 |
| EP | 1 378 255 | A2 | 1/2004 |
| GB | 0 942 305 | A | 11/1963 |
| GB | 0 983 073 | A | 2/1965 |
| GB | 2 314 840 | A | 6/1996 |
| GB | 2 314 842 | A | 1/1998 |
| GB | 2 344 519 | A | 6/2000 |
| IN | 159332 | | 5/1987 |
| JP | 6087225 | A | 5/1985 |
| RU | 2146264 | C1 | 3/2000 |
| RU | 02235539 | C1 | 9/2004 |
| WO | WO96/16643 | A | 6/1996 |
| WO | WO96/40033 | A1 | 12/1996 |
| WO | WO98/00180 | A1 | 1/1998 |
| WO | WO98/00446 | A | 1/1998 |
| WO | WO98/33479 | A | 8/1998 |
| WO | WO99/01166 | A1 | 1/1999 |
| WO | WO 01/22059 | A2 | 3/2001 |
| WO | WO 01/23653 | A1 | 4/2001 |
| WO | WO 02/02155 | A1 | 1/2002 |
| WO | WO 02/22059 | A1 | 3/2002 |
| WO | WO 02/058750 | A2 | 8/2002 |
| WO | WO 03/020191 | A | 3/2003 |

OTHER PUBLICATIONS

European Search Report dated Jul. 8, 2004, for corresponding EP application 03254091.6.

European Search Report dated Apr. 2, 2004 for corresponding EP application 03254119.5.

ASTM (American Society for Testing and Materials), Designation: E11-87, "Standard Specification for Wire-Cloth Sieves for Testing Purposes" pp. 13-16 (1987).

Turaev et al., "Hemostatic Activity and Reabsorbability of Carboxymethyl Cellulose", Khim.-Farm. Zh., 24(8). pp. 47-51 (1990) (English Abstract).

Ernest L. Jackson et al. J. Am. Chem. Soc, (1937), 59, 2049-2050.

G. F. Davidson, The Journal of the Textile Institute Transactions (1940), 81-96.

Virginia K. Frantz et al. J. Am. Med. Assoc., (1945), 129, 798-801.

Virginia K. Frantz, The Bulletin, (1946), 22, 102-110.

O.N. Lucas, Journal of Oral Therapeutics and Pharmacology, vol. 3, No. 4, (1967), 262-268.

M. Singh, Journal of Biomedical Materials Research, vol. 15, (1981), 655-661.

Helene Matras, J. Oral Maxillofac Surg, vol. 43, (8), (1985), 605-611.

T. Jai Mangal Sinha et al. Biomater., Med. Devices, Artif. Organs (1985), 12(3-4), 273-87.

Arthur G. Arand et. al. Neurosurgery vol. 18, No. 2, (1986), 223-233.

Reginald L. Stilwell et al. Handbook of Biodegradable Polymers (1997), 291-306.

J. Vincent Edwards et al. Wound Rep. Reg. 9, (2001), 50-58.

HERCULES Aqualon® Sodium Carboxmethylcellulose Product Specifications No. 4116-4, 1997.

*HERCULES Aqualon® Sodium Carboxmethylcellulose Physical and Chemical Properties*, 1995.

X75 200μm  ⎯12

FIG. 16A
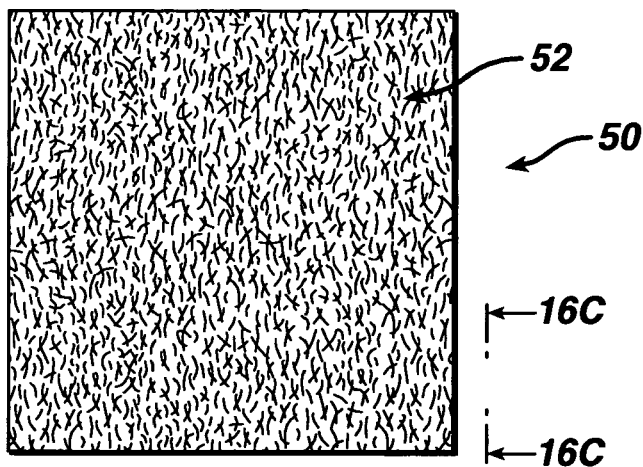
FIG. 16B
FIG. 16C
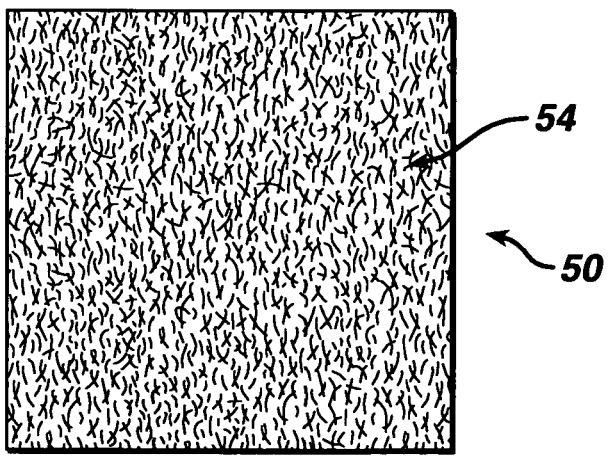
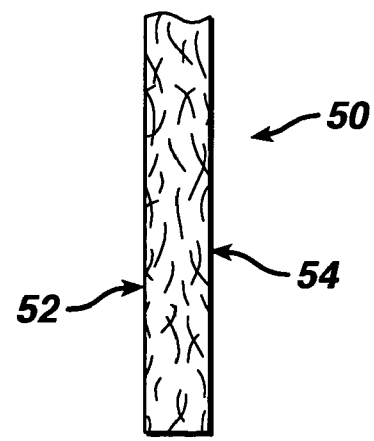

HEMOSTATIC WOUND DRESSINGS AND METHODS OF MAKING SAME

This application is a continuation-in-part of U.S. patent application Ser. No. 10/186,021, filed Jun. 28, 2002, U.S. patent application Ser No. 10/304,781, filed Nov. 26, 2002, now abandoned U.S. patent application Ser. No. 10/305,040, filed Nov. 26, 2002, now abandoned U.S. patent application Ser. No. 10/304,472, filed Nov. 26, 2002 now abandoned, and U.S. patent application Ser. No. 10/326,244, filed Dec. 20, 2002.

FIELD OF THE INVENTION

The present invention relates to hemostatic wound dressings containing a fabric substrate and a porous, water-soluble or water-swellable polymeric matrix disposed on and through the substrate and to methods of making such hemostatic wound dressings.

BACKGROUND OF THE INVENTION

The control of bleeding is essential and critical in surgical procedures to minimize blood loss, to reduce post-surgical complications, and to shorten the duration of the surgery in the operating room. Due to its biodegradability and its bactericidal and hemostatic properties, cellulose that has been oxidized to contain carboxylic acid moieties, hereinafter referred to as carboxylic-oxidized cellulose, has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures.

Currently utilized hemostatic wound dressings include knitted or non-woven fabrics comprising carboxylic-oxidized cellulose. Currently utilized oxidized regenerated cellulose is carboxylic-oxidized cellulose comprising reactive carboxylic acid groups and which has been treated to increase homogeneity of the cellulose fiber. Examples of such hemostatic wound dressings commercially available include Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company. Other examples of commercial absorbable hemostats containing carboxylic-oxidized cellulose include Oxycel® absorbable cellulose surgical dressing from Becton Dickinson and Company, Morris Plains, N.J. The oxidized cellulose hemostats noted above are knitted fabrics having a porous structure effective for providing hemostasis. They exhibit good tensile and compressive strength and are flexible such that a physician can effectively place the hemostat in position and maneuver the dressing during the particular procedure being performed.

Wound dressings utilizing carboxylic-oxidized cellulose, due to its acidic pH, are known to rapidly denature acid-sensitive, hemostatic proteins, including thrombin or fibrinogen, on contact. Thus, it is problematic to use the carboxylic-oxidized cellulose as a carrier for acid-sensitive species, such as thrombin and fibrinogen, as well as other acid-sensitive biologics and pharmaceutical agents.

In addition to issues concerning compatibility of conventional carboxylic-oxidized cellulose with "acid-sensitive" species, e.g. proteins, drugs, etc., while the absorbency of body fluid and the hemostatic action of such currently available carboxylic-oxidized cellulose hemostats are adequate for applications where mild to moderate bleeding is encountered, they are not known to be effective to provide and maintain hemostasis in cases of severe bleeding where a relatively high volume of blood is lost at a relatively high rate. In such instances, e.g. arterial puncture, liver resection, blunt liver trauma, blunt spleen trauma, aortic aneurysm, bleeding from patients with over-anticoagulation, or patients with coagulopathies, such as hemophilia, etc., a higher degree of hemostasis is required quickly.

In an effort to achieve enhanced hemostatic properties, blood-clotting agents, such as thrombin, fibrin and fibrinogen have been combined with other carriers or substrates for such agents, including gelatin-based carriers and a collagen matrix. Hemostatic wound dressings containing neutralized carboxylic-oxidized cellulose and protein-based hemostatic agents, such as thrombin, fibrinogen and fibrin are known. Neutralized carboxylic-oxidized cellulose is prepared by treating the carboxylic-oxidized cellulose with a water solution or alcohol solution of a basic salt of a weak organic acid to elevate the pH of the carboxylic-oxidized cellulose to between 5 and 8 by neutralizing the acid groups on the cellulose prior to addition of thrombin in order to make it thrombin-compatible. While such neutralized cellulose may be thrombin compatible, it is no longer bactericidal, as the anti-microbial activity of the carboxylic-oxidized cellulose provided by its acidic nature is lost.

Hemostatic agents such as thrombin, fibrinogen or fibrin, if not effectively bound chemically or physically to the substrate, may be rinsed away by blood at a wound site. The unbound agent may migrate into the blood stream, which is undesired. Methods of producing highly oxidized tri-carboxylic acid derivatives of cellulose as hemostatic materials, involving two-stage oxidation by successive processing with an iodine-containing compound and nitrogen oxides, has been disclosed in RU2146264 and IN159322. As disclosed in these disclosures, oxidized cellulosic materials were prepared by preliminary oxidation with metaperiodate or periodic acid to yield periodate-oxidized, dialdehyde cellulose to form the intermediate for forming carboxylic-oxidized cellulose. The dialdehyde cellulose intermediate then is further oxidized by $NO_2$ to yield the carboxylic-oxidized cellulose, which then is used as a hemostatic, anti-microbial and wound-healing agent.

It would be advantageous to provide a hemostatic wound dressing that not only provides hemostasis and anti-microbial properties similar to or better than conventional carboxylic-oxidized cellulose-containing hemostatic wound dressings and that also is compatible with "acid-sensitive" species, but that does so without the risk of hemostatic agents migrating into the blood stream.

It also would be advantageous to provide hemostatic wound dressings that provide and maintain hemostasis in cases of severe bleeding and that maintain physical properties required for use as a wound dressing, including strength and flexibility necessary for placement and maneuvering in or on the body by a physician. It also would be advantageous to provide methods of making such wound dressings that enable efficient and economic production of such dressings, such that the dressings may be manufactured on a commercial scale.

The present invention provides wound dressings that provide hemostatic and anti-microbial properties equivalent to or better than conventional carboxylic-oxidized cellulose-based hemostatic wound dressings, and/or that also may be compatible with "acid-sensitive" species, and improved methods for preparing such wound dressings.

SUMMARY OF THE INVENTION

The present invention is directed to hemostatic wound dressings comprising a fabric substrate, said fabric substrate comprising a first surface and a second surface opposing said first surface, said fabric substrate comprising fibers and having flexibility, strength and porosity effective for use as a hemostat, said fabric comprising biocompatible carboxylic-oxidized cellulose; and a porous, polymeric matrix substantially homogeneously distributed on said first surface and said second surface and through said fabric substrate, said porous, polymeric matrix comprising a biocompatible, water-soluble or water-swellable cellulose polymer, wherein prior to distribution of said polymeric matrix on and through said fabric substrate, said fabric substrate comprises about 3 percent by weight or more of water-soluble oligosaccharides; and to methods of making such wound dressings.

BRIEF DESCRIPTION OF THE FIGURES

FIG. 16a is a plan view of the first surface of a wound dressing prepared according to the method of the present invention.

FIG. 16b is a plan view of the second surface of a wound dressing prepared according to the method of the present invention.

FIG. 16c is an enlarged fragmentary side view as seen along view line 16C-16C of a wound dressing prepared according to the method of the present invention.

DETAILED DESCRIPTION OF THE INVENTION

Figure 1:
FIG. 1 is a scanning electron microscopy image (×75) of a cross section of a comparative wound dressing.

We have discovered certain hemostatic wound dressings that utilize a fabric as a substrate, where the fabric substrate comprises fibers prepared from a biocompatible polymer(s), comprises a first surface, a second surface opposing the first surface, and that possesses properties suitable for use as a hemostat, e.g. strength, flexibility and porosity. A more detailed description of such fabric properties is presented herein below. The wound dressings further comprise a porous, polymeric matrix substantially homogeneously dispersed on the first and second surfaces and through the fabric substrate. Either of the first and second surfaces may be used to contact the wound. The hemostatic wound dressings of the present invention provide and maintain effective hemostasis when applied to a wound requiring hemostasis. Effective hemostasis, as used herein, is the ability to control and/or abate capillary, venous, or arteriole bleeding within an effective time, as recognized by those skilled in the art of hemostasis. Further indications of effective hemostasis may be provided by governmental regulatory standards and the like.

Fabrics utilized in conventional hemostatic wound dressings, such as Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company, as well as Oxycel® absorbable cellulose surgical dressing from Becton Dickinson and Company, Morris Plains, N.J., all may be used in preparing wound dressings according to the present invention. In certain embodiments, wound dressings of the present invention are effective in providing and maintaining hemostasis in cases of severe bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia.

Such wound dressings allow a patient to ambulate quicker than the current standard of care following, e.g. a diagnostic or interventional endovascular procedure.

In certain embodiments of the invention, the wound dressings may further include a hemostatic agent, or other biological or therapeutic compounds, moieties or species, including drugs and pharmaceutical agents as described in more detail herein below. The agents may be bound within the polymeric matrix, as well as to the fabric surfaces and/or within the fabric. The agents may be bound by chemical or physical means, provided that they are bound such that they do not migrate from the wound dressing upon contact with blood in the body. The hemostatic agent may be dispersed partially or homogenously through the fabric and/or the polymeric matrix. In some embodiments of the invention, the hemostatic agents, or other biological or therapeutic compounds, moieties or species, e.g. drugs, and pharmaceutical agents, may be "acid-sensitive", meaning that they may be degraded or denatured by, or otherwise detrimentally affected by acidic pH, such as is provided by conventional carboxylic-oxidized hemostatic wound dressings.

The fabric substrates utilized in the present invention may be woven or nonwoven, provided that the fabric possesses the physical properties necessary for use in hemostatic wound dressings. A preferred woven fabric has a dense, knitted structure that provides form and shape for the hemostatic wound dressings. Such fabrics are described in U.S. Pat. No. 4,626,253, the contents of which is hereby incorporated by reference herein as if set forth in its entirety.

In preferred embodiments of the present invention, the absorbable hemostatic fabrics are warp knitted tricot fabrics constructed of bright rayon yarn which is subsequently oxidized to include carboxyl or aldehyde moieties in amounts effective to provide the fabrics with biodegradability and anti-microbial activity. The fabrics are characterized by having a single ply thickness of at least about 0.5 mm, a density of at least about 0.03 $g/cm^2$, air porosity of less than about 150 $cm^3/sec/cm^2$, and liquid absorption capacity of at least about 3 times the dry weight of the fabric and at least about 0.1 g water per $cm^2$ of the fabric.

The knitted fabrics have good bulk without undue weight, are soft and drapable, and conform well to the configuration of the surface to which they are applied. The fabric may be cut into suitable sizes and shapes without running or fraying along the cut edge. Fabric strength after oxidation is adequate for use as a surgical hemostat.

Preferred hemostatic fabrics used in the present invention comprise oxidized cellulose and are best characterized by their physical properties of thickness, bulk, porosity and liquid absorption capacity, as recited above. Suitable fabrics having these properties may be constructed by knitting 60 denier, 18-filament bright rayon yarn on a 32-gauge machine at a knit quality of 12. A suitable tricot fabric construction is front-bar 1-0, 10-11; back-bar 2-3, 1-0. The extended shog movement imparted to the front bar results in a 188 inch runner compared to a 70 inch runner for the back guide bar, and increases the fabric bulk and density. The ratio of front to back bar runners in this particular construction is 1:2.7.

Typical physical and hemostatic properties of preferred fabrics produced as described above are noted in Table 1.

TABLE I

| Property | |
|---|---|
| Thickness (mm); | 0.645 |
| Density ($g/cm^2$); | 0.052 |

TABLE I-continued

| Property | |
|---|---|
| Air Porosity ($cm^3/sec/cm^2$); | 62.8 |
| Tensile Strength[1] (md/cd)Kg; | 1.9/4.5 |
| Elongation[2] (%); | 23/49 |
| Absorption[3] | |
| (g/g fabric); | 3.88 |
| ($g/cm^2$ fabric); | 0.20 |
| Hemostasis[4] (min) | |
| 1 ply; | 5.7 ± 1.0 |
| 2 ply; | 5.6 ± 1.8 |

[1]tensile strength determined at 2 in/min extension md/cd = machine direction/cross direction.
[2]Elongation, machine direction/cross direction.
[3]Absorption based on weight of water absorbed by fabric.
[4]Hemostasis evaluation on incised porcine splenic wounds, time to stop bleeding.

The tricot fabrics utilized in the present invention may be constructed from bright rayon yarns of from about 40 to 80 total denier. Each yarn may contain from 10 to 25 individual filaments, although each individual filament preferably is less than 5 denier to avoid extended absorption times. The high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, further increases fabric thickness and density.

Other warp knit tricot fabric constructions which produce equivalent physical properties may, of course, be utilized in the manufacture of the improved hemostatic fabrics and wound dressings of the present invention, and such constructions will be apparent to those skilled in the art.

Polymers useful in preparing the fabric substrates in wound dressings of the present invention include, without limitation, collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly (alkylene oxide), polyalkylenes, polythioesters, polythioethers, polyvinyls, polymers comprising lipids, and mixtures thereof. Preferred fibers comprise oxidized regenerated polysaccharides, in particular oxidized regenerated cellulose.

Preferably, oxidized polysaccharides are used to prepare wound dressings of the present invention. More preferably, oxizided cellulose is used to prepare fabrics used in wound dressings of the present invention. The cellulose either may be carboxylic-oxidized cellulose, or may be aldehyde-oxidized cellulose, each as defined and described herein. Even more preferably, oxidized regenerated cellulose is used to prepare fabric substrates used in wound dressings of the present invention. Regenerated cellulose is preferred due to its higher degree of uniformity versus cellulose that has not been regenerated. Regenerated cellulose and a detailed description of how to make regenerated oxidized cellulose is set forth in U.S. Pat. No. 3,364,200 and U.S. Pat. No. 5,180,398, the contents each of which is hereby incorporated by reference as if set forth in its entirety. As such, teachings concerning regenerated oxidized cellulose and methods of making same are well within the knowledge of one skilled in the art of hemostatic wound dressings.

Certain of the wound dressings of the present invention utilize fabric substrates that have been oxidized to contain carboxyl moieties in amounts effective to provide the fabrics with biodegradability and anti-microbial activity. U.S. Pat. 3,364,200 discloses the preparation of carboxylic-oxidized cellulose with an oxidizing agent such as dinitrogen tetroxide in a Freon medium. U.S. Pat. No. 5,180,398 discloses the preparation of carboxylic-oxidized cellulose with an oxidizing agent such as nitrogen dioxide in a per-fluorocarbon solvent. After oxidation by either method, the fabric is thoroughly washed with a solvent such as carbon tetrachloride, followed by aqueous solution of 50 percent isopropyl alcohol (IPA), and finally with 99% IPA. Prior to oxidation, the fabric is constructed in the desired woven or nonwoven construct suitable for use as a hemostat. Certain wound dressings according to the present invention that utilize such fabrics have been found to provide and maintain hemostasis in cases of severe bleeding.

Where the fabric substrate comprises carboxylic-oxidized cellulose, it has been found that the fabric preferably is conditioned prior to saturation with polymer solution and lyophilization in order to provide homogenous distribution of the polymer solution on and through the fabric substrate. Conditioning of the fabric can be achieved by storing the fabric at room temperature under ambient conditions for at least 6 months, or conditioning of the fabric can be accelerated. Preferably, the fabric is exposed to conditions of about 4° C. to about 90° C., at a relative humidity of from about 5% to about 90%, for a time of from about 1 hour to 48 months. More preferably, the fabric is exposed to conditions of about 4° C. to about 60° C., at a relative humidity of from about 30% to about 90%, for a time of from about 72 hours to 48 months. Even more preferably, the fabric is exposed to conditions of about 18° C. to about 50° C., at a relative humidity of from about 60% to about 80%, for a time of from about 72 hours to 366 hours. Most preferably, the fabric is conditioned at a temperature of about 50° C., at a relative humidity of about 70%, for a time of about 168 hours. The fabric may be placed horizontally in a conditioned environment, taking care to provide spacing between the fabric substrates to allow proper conditioning. The fabric also may be suspended vertically to allow conditioning.

As result of the conditioning of the carboxylic-oxidized cellulose fabric substrate, the fabric substrate will comprise at least about 3 weight percent of water-soluble molecules, preferably from about 3 to about 30 weight percent, more preferably from about 8 to about 20 weight percent, even more preferably from about 9 to about 12 weight percent, and most preferably about 10 weight percent. In general, the water-soluble molecules are acid-substituted oligosaccharides containing approximately 5 or fewer saccharide rings. It has been found that the hemostatic efficacy of the wound dressing containing such carboxylic-oxidized cellulose fabric substrates, including the occurrence of re-bleeding of a wound for which hemostasis initially has been achieved, is improved when the contents of the water-soluble molecules reach about 8%, preferably about 10%, based on the weight of the fabric substrate.

Fabric substrates used in the present invention also will comprise from about 3 to about 20 weight percent of water, preferably from about 7 to about 13 weight percent, and more preferably from about 9 to about 12 weight percent water.

Similar levels of moisture and water-soluble molecules in the carboxylic-oxidized cellulose fabric substrate also may be achieved by other means. For example, sterilization of the fabric by know techniques, such as gamma or e-beam irradiation, may provide similar content of water and/or water-soluble molecules. In addition, water-soluble molecules such as oligosacchrides could be added to the fabric prior to distribution of the porous, polymeric matrix on and through the fabric. Once having the benefit of this disclosure, those skilled in the art may readily ascertain other methods for providing such fabrics with moisture and/or water-soluble molecules.

Wound dressings of the present invention that are compatible with acid-sensitive species comprise fabric substrates prepared from a biocompatible, aldehyde-oxidized polysaccharide. In such wound dressings, the polysaccharide preferably will contain an amount of aldehyde moieties effective to render the modified polysaccharide biodegradable, meaning that the polysaccharide is degradable by the body into components that either are resorbable by the body, or that can be passed readily by the body. More particularly, the biodegraded components do not elicit permanent chronic foreign body reaction when they are absorbed by the body, such that no permanent trace or residual of the component is retained at the implantation site.

Aldehyde-oxidized polysaccharides used in the present invention may include, without limitation, cellulose, cellulose derivatives, e.g. alkyl cellulose, for instance methyl cellulose, hydroxyalkyl cellulose, alkylhydroxyalkyl cellulose, cellulose sulfate, salts of carboxymethyl cellulose, carboxymethyl cellulose and carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, heparin, heparin sulfate, heparan, heparan sulfate, dermatan sulfate, keratin sulfate, carrageenans, chitosan, starch, amylose, amylopectin, poly-N-glucosamine, polymannuronic acid, polyglucuronic acid, polyguluronic acid and derivatives of the above, each of which has been oxidized to included anti-microbial effective amounts of aldehyde moieties.

In preferred embodiments utilizing aldehyde-oxidized polysaccharides, the polysaccharide is oxidized as described herein to assure that the aldehyde-oxidized polysaccharide is biodegradable. Such biodegradable, aldehyde-oxidized polysaccharides may be represented by Structure I below.

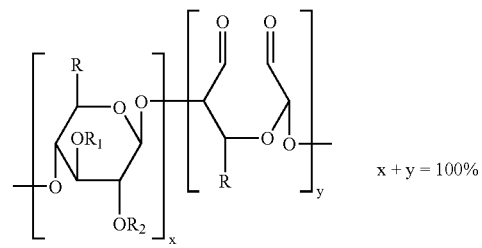

where x and y represent mole percent, x plus y equals 100 percent, x is from about 95 to about 5, y is from about 5 to about 95; and R may be $CH_2OR_3$, $COOR_4$, sulphonic acid, or phosphonic acid; $R_3$ and $R_4$ may be H, alkyl, aryl, alkoxy or aryloxy, and $R_1$ and $R_2$ may be H, alkyl, aryl, alkoxy, aryloxy, sulphonyl or phosphoryl.

In certain embodiments of the present invention, the biocompatible, biodegradable hemostatic wound dressing comprises a fabric substrate prepared from a biocompatible, biodegradable, aldehyde-oxidized regenerated cellulose. In particular, preferred aldehyde-oxidized regenerated cellulose is one comprising repeating units of Structure II:

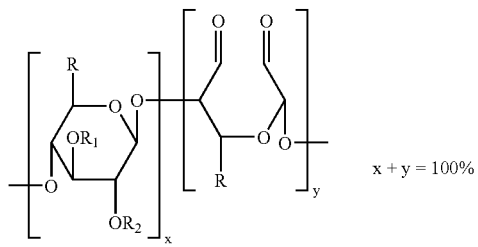

where x and y represent mole percent, x plus y equals 100 percent, x is from about 95 to about 5, y is from about 5 to about 95; and R is $CH_2OH$, $R_1$ and $R_2$ are H.

In preferred embodiments of the invention, the aldehyde-oxidized regenerated polysaccharide, e.g. cellulose, is essentially free of functional or reactive moieties other than aldehyde moieties. By essentially free, it is meant that the polysaccharide does not contain such functional or reactive moieties in amounts effective to alter the properties of the aldehyde-oxidized polysaccharide, or to provide the fabric comprising the polysaccharide with a pH of less than about 4.5, more preferably less than about 5, or greater than about 9, preferably about 9.5. Such moieties include, without limitation, carboxylic acid moieties typically present in wound dressings made from carboxyl-oxidized cellulose. Excess levels of carboxylic acid moieties will lower the pH of the fabrics and dressings so that they are not compatible for use with those acid-sensitive species that may be degraded or denatured by such a low pH, e.g. thrombin. Other moieties essentially excluded include, without limitation, sulfonyl or phosphonyl moieties.

As noted above, wound dressings of the present invention comprise a porous, polymeric matrix dispersed substantially homogenously on the first and second surfaces and through the fabric substrate. The polymer used to prepare the porous, polymeric matrix in wound dressings of the present invention is a biocompatible, water-soluble, or water-swellable polymer. The water-soluble or water-swellable polymer rapidly absorbs blood or other body fluids and forms a tacky or sticky gel adhered to tissue when placed in contact therewith. The fluid-absorbing polymer, when in a dry or concentrated state, interacts with body fluid through a hydration process. Once applied in a bleeding site, the polymer interacts with the water component in the blood via the hydration process. The hydration force provides an adhesive interaction that aids the hemostat adhere to the bleeding site. The adhesion creates a sealing layer between the hemostat and the bleeding site to stop the blood flow.

Preferred polymers used to fabricate the matrices include polysaccharides. Such polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. The composite hemostat of the present invention remains very flexible, conforms to a bleeding site and retains good tensile and compressive strength to withstand handling during application. The hemostat can be cut into different sizes and shapes to fit the surgical needs. It can be rolled up or packed into irregular anatomic areas. The fabric in a preferred embodiment capable of providing and maintaining hemostasis in cases of severe bleeding is a knitted carboxylic-oxidized regenerated cellulose, such as the fabric used to manufacture Surgicel Nu-Knit® absorbable hemostat available from Ethicon, Inc., Somerville, N.J.

As noted above, in certain embodiments of the invention, a biologics, a drug, a hemostatic agent, a pharmaceutical agent, or combinations thereof, that otherwise may be sensitive to the low pH of conventional carboxyl-oxidized cellulose-containing wound dressings, may be incorporated into wound dressings of the present invention without having to adjust pH prior to incorporation into the dressing. To fabricate such a hemostatic wound dressing, a drug or agent may be dissolved in an appropriate solvent. The fabric may then be coated with the drug solution and the solvent removed. Preferred biologics, drugs and agent include analgesics, anti-infective agents, antibiotics, adhesion preventive agents, pro-coagulants, and wound healing growth factors.

Hemostatic agents that may be used in wound dressings according to the present invention include, without limitation, procoagulant enzymes, proteins and peptides, can be naturally occurring, recombinant, or synthetic, and may be selected from the group consisting of prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. Preferred hemostatic agents used in the present invention are thrombin, fibrinogen and fibrin.

Protein-based hemostatic agents, such as thrombin, fibrin or fibrinogen, if bound to the wound dressing, can enhance the hemostatic property of aldehyde-oxidized regenerated cellulose wound dressings and reduce the risk of thrombosis caused by free hemostatic agents migrating into the blood stream. Hemostatic agents may be bound to the wound dressings either by chemical of physical means. Agents may be covalently conjugated with aldehyde groups pendant from the polysaccharide in one instance, thus chemically binding the agent to the wound dressing. Preferably, the hemostatic agents are physically bound to the wound dressing via incorporation into the polymeric matrix dispersed on and through the aldehyde-oxidized polysaccharide fabric and immobilized, i.e. bound, via lyophilization.

Such hemostatic wound dressings of the present invention comprise hemostatic agents, including but not limited to thrombin, fibrinogen or fibrin, in an amount effective to provide rapid hemostasis and maintain effective hemostasis in cases of severe bleeding. If the concentration of the hemostatic agent in the wound dressing is too low, the hemostatic agent does not provide an effective proagulant activity to promote rapid clot formation upon contact with blood or blood plasma. A preferred concentration range of thrombin in the wound dressing is from about 0.001 to about 1 percent by weight. A more preferred concentration of thrombin in the wound dressing is from about 0.01 to about 0.1 percent by weight. A preferred concentration range of fibrinogen in the wound dressing is from about 0.1 to about 50 percent by weight. A more preferred concentration of fibrinogen in the wound dressing is from about 2.5 to about 10 by weight. A preferred concentration range of fibrin in the wound dressing is from about 0.1 to about 50 percent by weight. A more preferred concentration of fibrin in the wound dressing is from about 2.5 to about 10 by weight.

In certain embodiments, fabrics used in wound dressings of the present invention may comprise covalently conjugated there with a hemostatic agent bearing an aldehyde-reactive moiety. In such embodiments, the aldehyde moiety of aldehyde-oxidized regenerated polysaccharide can readily react with the amine groups present on the amino acid side chains or N-terminal residues of thrombin, fibrinogen or fibrin, resulting in forming a conjugate of the hemostatic agent with the aldehyde-oxidized regenerated polysaccharide covalently linked by a reversible imine bond. The imine bonded aldehyde-oxidized regenerated polysaccharide/hemostatic agent conjugate may then be further reacted with a reducing agent such as sodium borohydride or sodium cyanoborohydride to form an irreversible secondary amine linkage. In such embodiments of the invention, the hemostatic agent is dispersed at least on the surface of the fabric, and preferably at least partially through the fabric structure, bound reversibly or irreversibly to the aldehyde-oxidized polysaccharide.

Oxidation of 2,3-vicinal hydroxyl groups in a carbohydrate with periodic acid (or any alkali metal salt thereof) forms a di-aldehyde or di-aldehyde derivatives. These aldehyde moieties(—RCH(O)) can then readily react with a primary amine moiety (—NH$_2$), such as are present on the amino acid side chains or N-terminal residues of proteins, resulting in an equilibrium with the reaction product, a protein and carbohydrate conjugate, covalently linked by a relatively unstable and reversible imine moiety (—N═CHR). To stabilize the linkage between the biomolecule and the substrate surface, subsequent reductive alkylation of the imine moiety is carried out using reducing agents (i.e., stabilizing agents) such as, for example, sodium borohydride, sodium cyanoborohydride, and amine boranes, to form a secondary amine (—NH—CH$_2$—R). The features of such hemostatic agents conjugated with the aldehyde-oxidized regenerated cellulose wound dressing can be controlled to suit a desired application by choosing the conditions to form the composite hemostat during conjugation.

In such embodiments of the present invention, the hemostatic agent, such as thrombin, fibrinogen or fibrin, is dispersed substantially homogeneously through the wound dressing fabric. In such cases, aldehyde-oxidized regenerated cellulose fabric may be immersed in the solution of thrombin, fibrinogen or fibrin to provide homogeneous distribution throughout the wound dressing.

In certain embodiments of the invention, the thrombin conjugate of aldehyde-oxidized regenerated cellulose fabric is further reacted with reducing agents such as sodium borohydride or sodium cyanoborohydride to form a secondary amine linkage. The aldehyde-oxidized regenerated cellulose fabric can be soaked with the desired amount of aqueous solution of thrombin, then reacted with aqueous solution of sodium borohydride or sodium cyanoborohydride reconstituted in phosphate buffer (PH═8) prior to lyophilization.

The reduced form of the aldehyde-oxidized regenerated cellulose-thrombin conjugate is more stable due to the nature of the secondary amine linkage. Hemostatic wound dressings of this embodiment have enhanced hemostatic properties, as well as increased stability, and can provide rapid hemostasis without causing thrombin to migrate into the blood stream and cause severe thrombosis.

In preferred embodiments of the present invention, the hemostatic agent, such as thrombin, fibrinogen, or fibrin is constituted in an aqueous solution of a non-acidic, water-soluble or water-swellable polymer, as described herein above, including but not limited to methyl cellulose, hydroxyalkyl cellulose, water-soluble chitosan, salts of carboxymethyl carboxyethyl cellulose, chitin, salts of hyaluronic acid, alginate, propylene glycol alginate, glycogen, dextran, carrageenans, chitosan, starch, amylose, poly-N-glucosamine, and the aldehyde-oxidized derivatives thereof. The aldehyde-oxidized regenerated cellulose fabric can be soaked with the desired amount of aqueous solution of hemostatic agent and the water-soluble or water-swellable polymer and rapidly lyophilized using known methods that retain therapeutic activity. When constructed thusly, the hemostatic agent will be substantially homogenously dispersed through the polymeric matrix formed during lyophilization.

One skilled in the art, once having the benefit of this disclosure, will be able to select the appropriate hemostatic agent, water-soluble or water-swellable polymer and solvent therefore, and levels of use of both the polymer and hemostatic agent, depending on the particular circumstances and properties required of the particular wound dressing.

One method of making the porous, polymeric matrix is to contact the fabric substrate with the appropriate amount of polymer solution, such that the dissolved polymer is disposed on the surfaces and substantially homogenously through the fabric, flash-freeze the polymer and fabric, and then remove the solvent from the frozen structure under vacuum, i.e. by lyophilization. The steps involved in the preparation of the novel porous structure comprise dissolving the appropriate polymer to be lyophilized in an appropriate solvent for the polymer to prepare a homogenous polymer solution. The fabric then is contacted with the polymer solution such that it is saturated with the polymer solution. The fabric substrate and polymer solution incorporated in the dense construct of the fabric then is subjected to a freezing and vacuum drying cycle. The freezing/drying step phase removes the solvent by sublimation, leaving a porous, polymer matrix structure disposed on and through the fabric substrate. Through this preferred lyophilization method, the wound dressing comprising a fabric substrate that comprises a matrix of the water-soluble or water-swellable polymer and having microporous and/or nanoporous structure is obtained. The lyophilization conditions are important to the novel porous structure in order to create a large matrix surface area in the hemostat with which body fluids can interact once the dressing is applied to a wound requiring hemostasis.

During the lyophilization process, several parameters and procedures are important to produce wound dressings having mechanical properties suitable for use in hemostatic wound dressings. The features of such microporous structure can be controlled to suit a desired application by choosing the appropriate conditions to form the composite hemostat during lyophilization. The type of microporous morphology developed during the lyophilization is a function of such factors, such as the solution thermodynamics, freezing rate, temperature to which it is frozen, and concentration of the solution. To maximize the surface area of the porous matrix of the present invention, a preferred method is to quickly freeze the fabric/polymer construct at lower than 0° C., preferably at about −50° C., and to remove the solvent under high vacuum. The porous matrix produced thereby provides a large fluid-absorbing capacity to the hemostatic wound dressing. When the hemostatic wound dressing comes into contact with body fluid, a very large surface area of polymer is exposed to the fluid instantly. The hydration force of the hemostat and subsequent formation of a tacky gelatinous layer helps to create an adhesive interaction between the hemostat and the bleeding site. The microporous structure of the polymeric matrix also allows blood to quickly pass through the fabric surface before the hydration takes place, thus providing an increased amount of the polymer to come in contact with the body fluids. The formation of a gelatinous sheet on oxidized cellulose upon blood contact will enhance the sealing property of the water-soluble gelatinous layer, which is critical to rapid hemostasis in cases ranging from moderate to severe bleeding.

The fabric substrate comprises the polymeric matrix in an amount effective to provide and maintain effective hemostasis, preferably in cases of severe bleeding. If the ratio of polymer to fabric is too low, the polymer does not provide an effective seal to physically block the bleeding, thus reducing the hemostatic properties. If the ratio is too high, the composite hemostat wound dressing will be too stiff or too brittle to conform to wound tissue in surgical applications, thus adversely affecting the mechanical properties necessary for handling by the physician in placement and manipulation of the dressing. Such an excessive ratio will also prevent the blood from quickly passing through the fabric surface to form the gelatinous layer on the oxidized cellulose that is critical for enhancing the sealing property. A preferred weight ratio of polymer to fabric is from about 1:99 to about 15:85. A more preferred weight ratio of polymer to fabric is from about 3:97 to about 10:90.

Wound dressings of the present invention are best exemplified in the figures prepared by scanning electron microscope. The samples were prepared by cutting 1-cm$^2$ sections of the dressings by using a razor. Micrographs of both the first surface and opposing second surface, and cross-sections were prepared and mounted on carbon stubs using carbon paint. The samples were gold-sputtered and examined by scanning electron microscopy (SEM) under high vacuum at 4 KV.

FIG. 1 is a cross-section view (75×) of uncoated carboxylic-oxidized regenerated cellulose fibers 12 organized as fiber bundles 14 and knitted into fabric 10 according to preferred embodiments of the invention discussed herein above. One commercial example of such a fabric is Surgicel Nu-Knit® absorbable hemostatic wound dressing.

Figure 2:
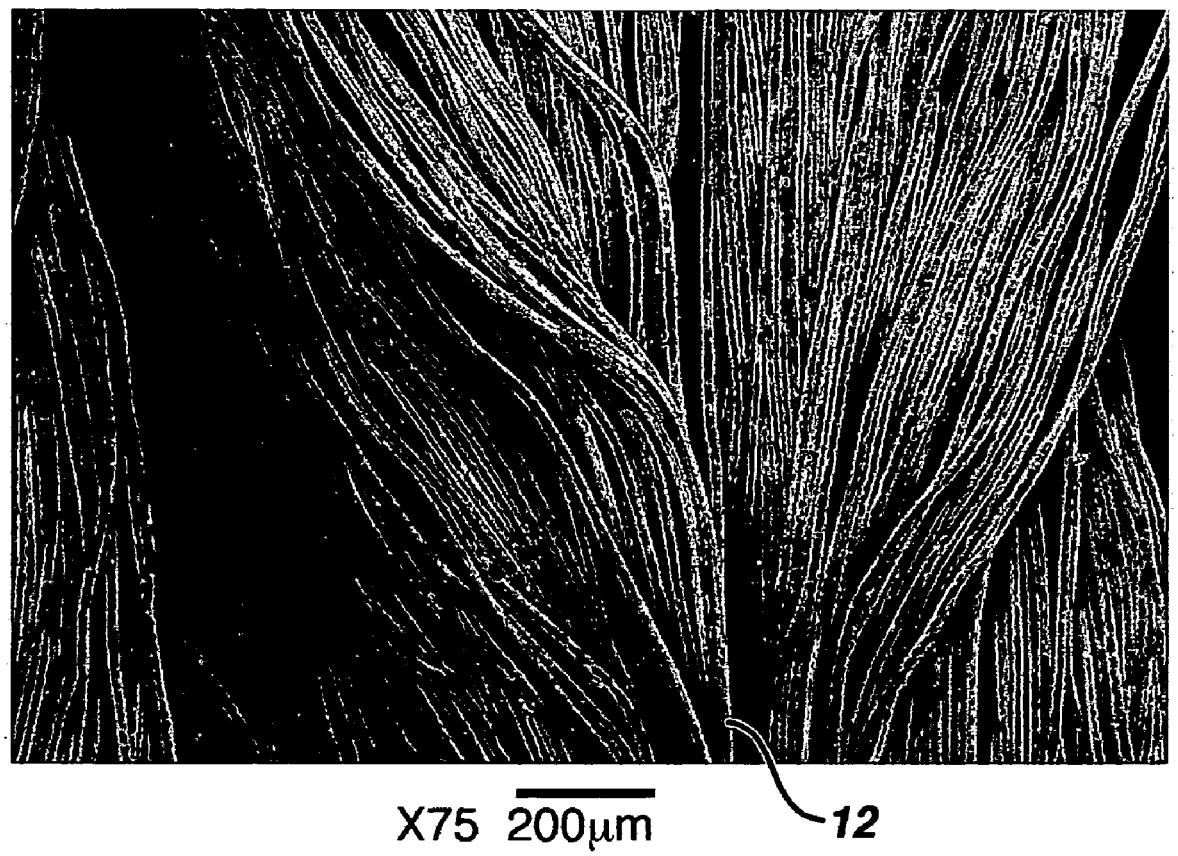
FIG. 2 is a scanning electron microscopy image (×75) of the first surface of a comparative wound dressing.

FIG. 2 is a view of a first surface of the fabric of FIG. 1. Individual fibers 12 are shown within a bundle.

Figure 3:
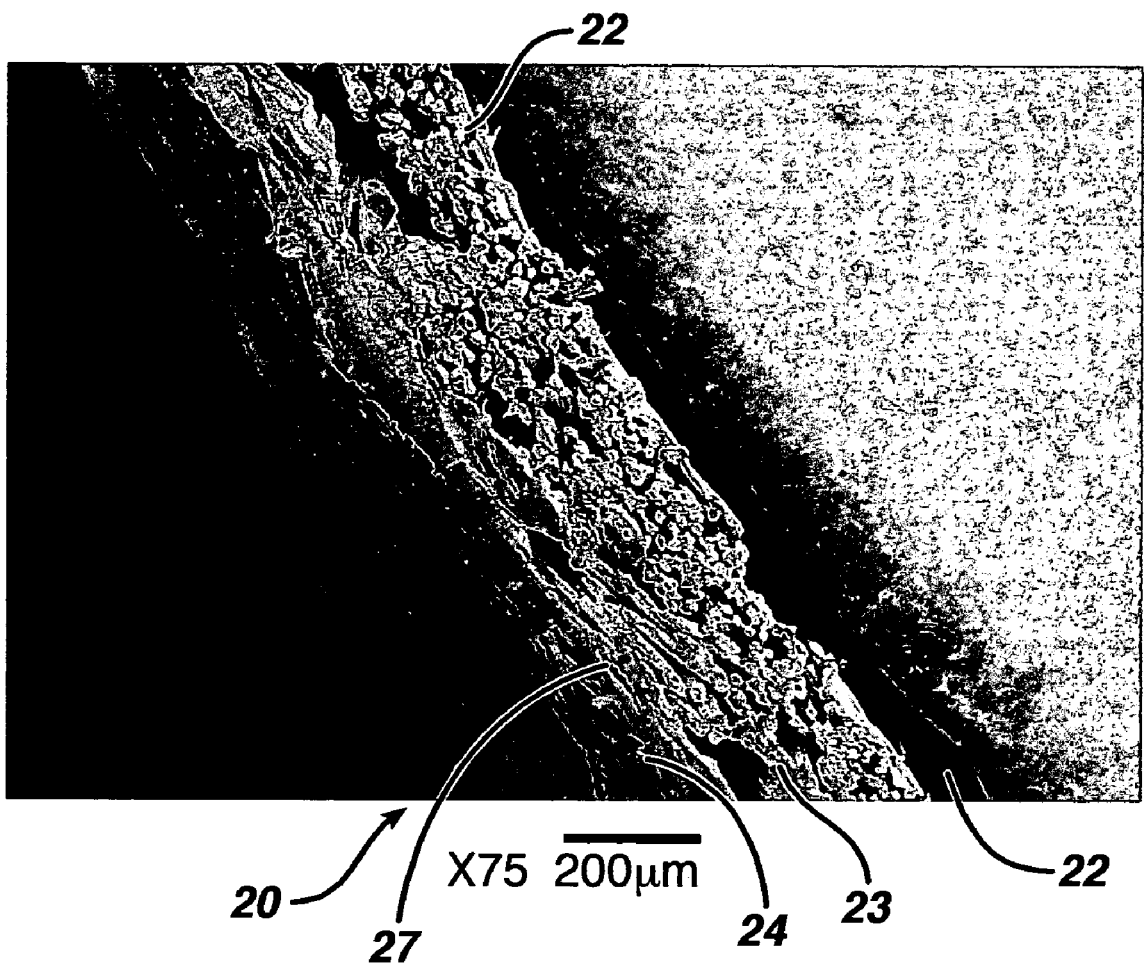
FIG. 3 is a scanning electron microscopy image (×75) of a cross section of a comparative wound dressing.

FIG. 3 is a cross-section view of fabric 20 having first surface 22 and opposing surface 24 and that has been coated with a solution of sodium carboxymethyl cellulose (Na—CMC) and then air dried as in Example 6. Individual fibers 23 also are shown.

Figure 4:
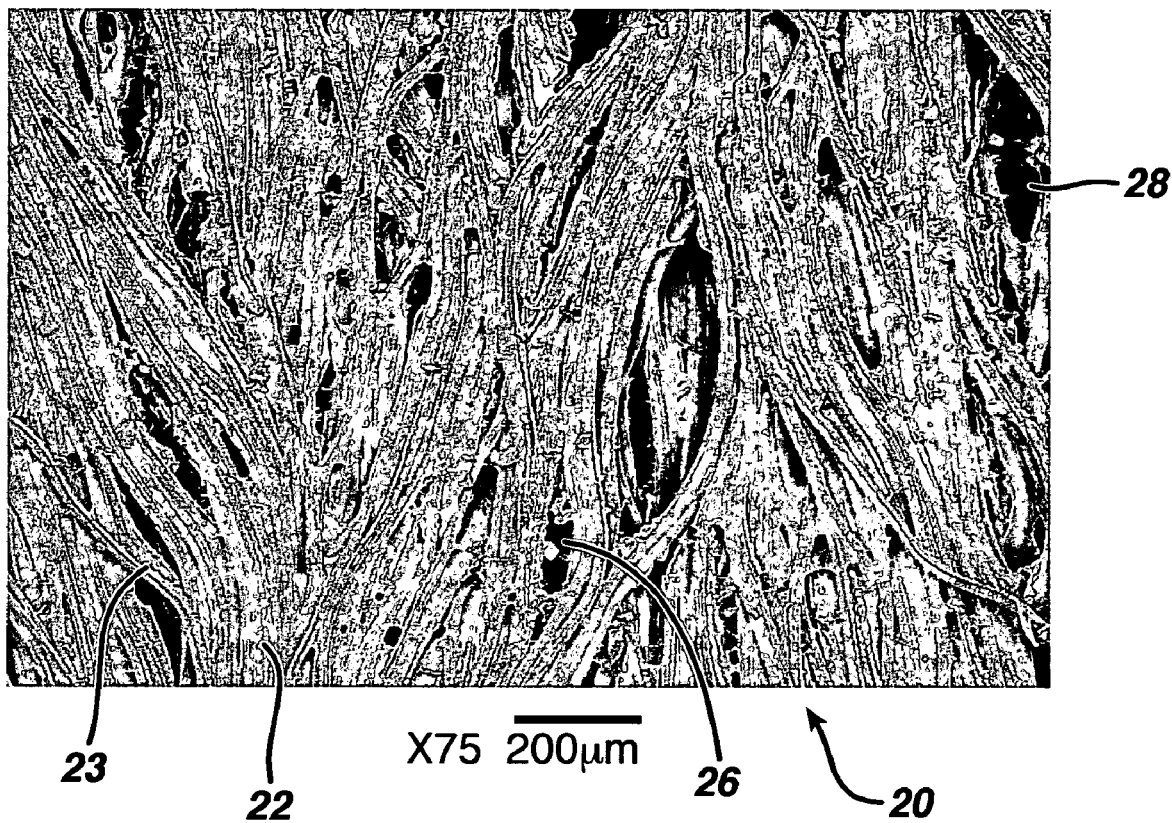
FIG. 4 is a scanning electron microscopy image (×75) of the first surface of a comparative wound dressing.

FIG. 4 is a view of surface 22 of fabric 20. As observed therein, in the course of air-drying, polymer 26 agglomerates and adheres to fibers 23, in many instances adhering fibers 23 one to the other and creating large voids 28 in the hemostatic fabric through which body fluids may pass. Polymer 26 dispersed on and through fabric 20 is not in the state of a porous matrix and thus provides no hemostasis in cases of severe bleeding as described herein above due, at least in part, to a lack of sufficient porosity, e.g. surface area, to provide polymer/body fluid interaction effective to provide and maintain hemostasis in cases of severe bleeding.

Figure 5:
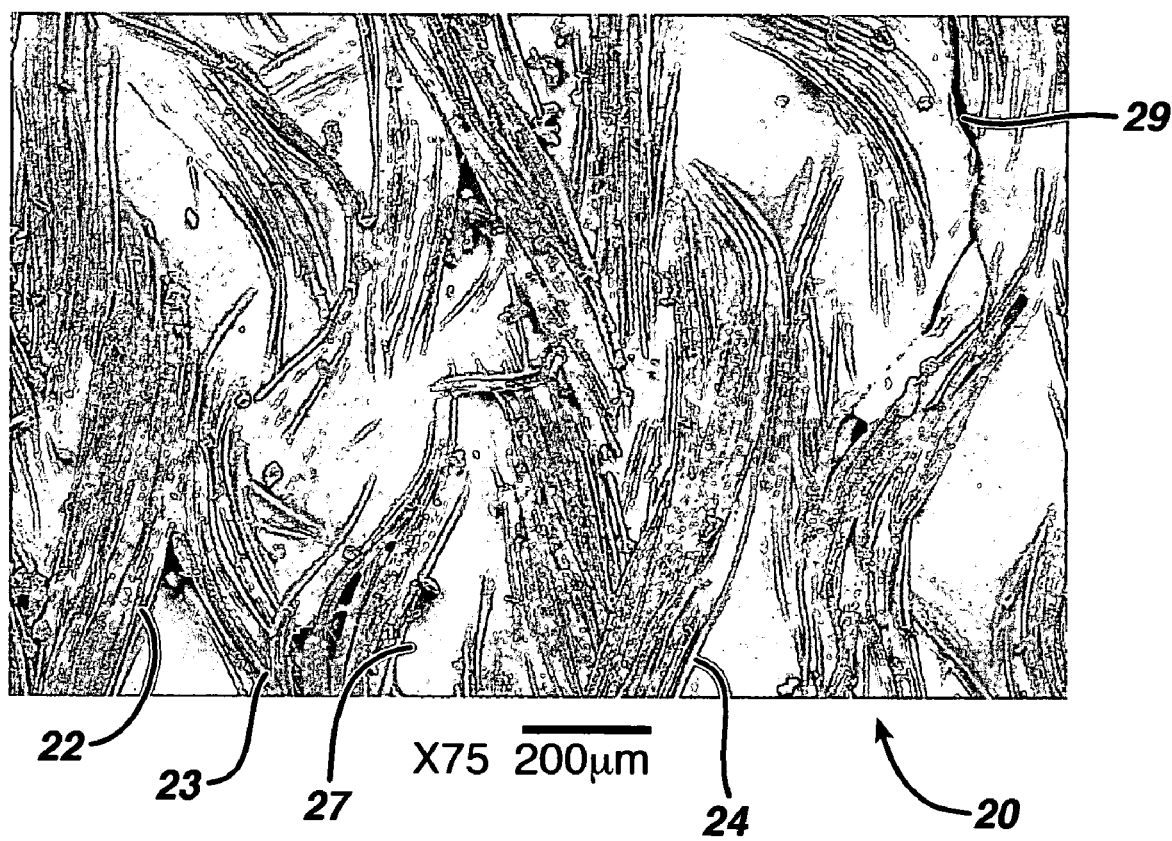
FIG. 5 is a scanning electron microscopy image (×75) of the second opposing surface of a comparative wound dressing.

FIG. 5 is a view of opposing surface 24 of fabric 20. As shown, opposing surface 24 contains a larger concentration of Na—CMC coating material as opposed to surface 22 shown in FIG. 4, obscuring most of fibers 23, although the knitting pattern could still be discerned. The coating was thick enough to span across all of the fibers and generate an intact layer 27 of its own, also shown in FIG. 3. This layer appeared to be brittle, as cracks 29 in the coating were observed. The coating layer thickness varied from as thin as about 3 microns in some sections to about 30-65 microns in other sections.

In comparing the surface morphologies of surface 22 and opposing surface 24 of fabric 20, it is apparent that surface 22 contained significantly less Na—CMC. The coating was significantly thinner on the fibers than the coating on the opposing surface. While some Na—CMC was observed to span across some fibers, the coating was incomplete or had perforations present. The coating layer thickness, where present, did not exceed about 2 microns.

It is clear from FIGS. 3-5 that the fabrics prepared by air-drying do not contain a porous, polymeric matrix homogenously dispersed on the surfaces and there through. As such, those fabrics do not provide and maintain hemostasis in cases of severe bleeding, as shown herein. In addition, such fabrics are brittle, stiff, do not conform to wound sites, are not able to be handled by physicians, and generally are not suitable for use as wound dressings in cases of severe bleeding.

Figure 6:
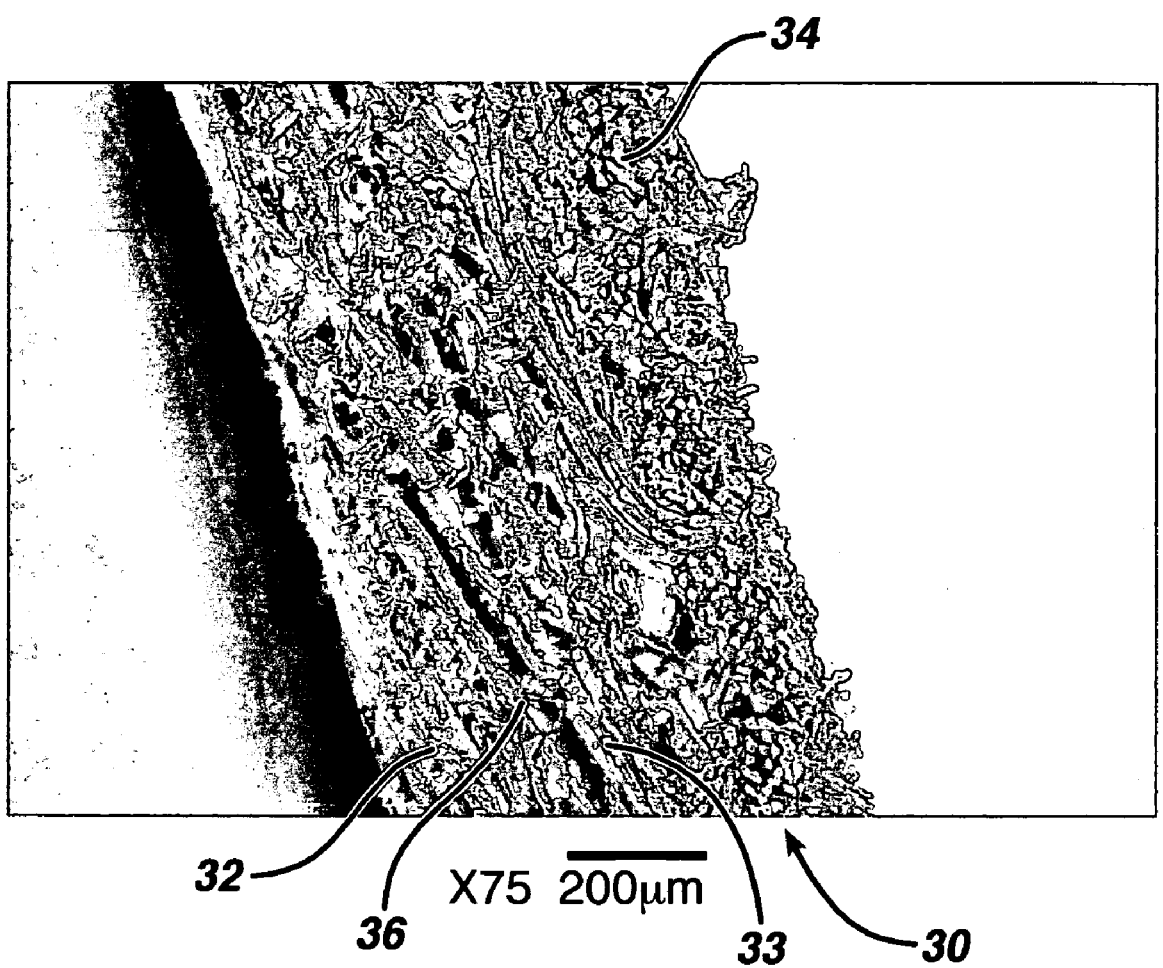
FIG. 6 is a scanning electron microscopy image (×75) of a cross-section of a wound dressing of the present invention.
Figure 7:
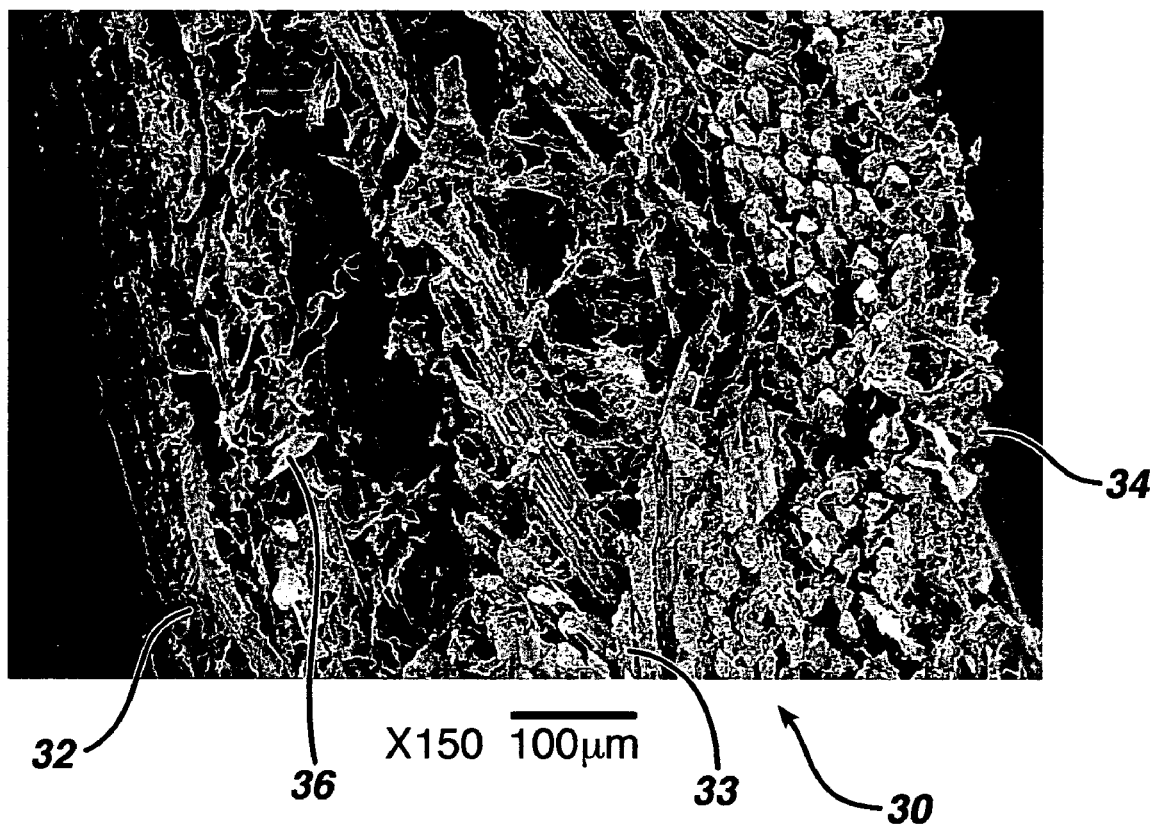
FIG. 7 is a scanning electron microscopy image (×150) of a cross-section of a wound dressing of the present invention.

Hemostatic fabrics according to the present invention are set forth in FIGS. 6-9. As shown in FIGS. 6 and 7, a porous, polymer matrix is more substantially homogenously distributed on surface 32 and throughout fabric 30. Polymer 36 forms a porous matrix integrated with knitted fibers 33. The porous polymer matrix exhibits significant liquid absorption properties from capillary action in the same manner as a sponge.

Figure 8:
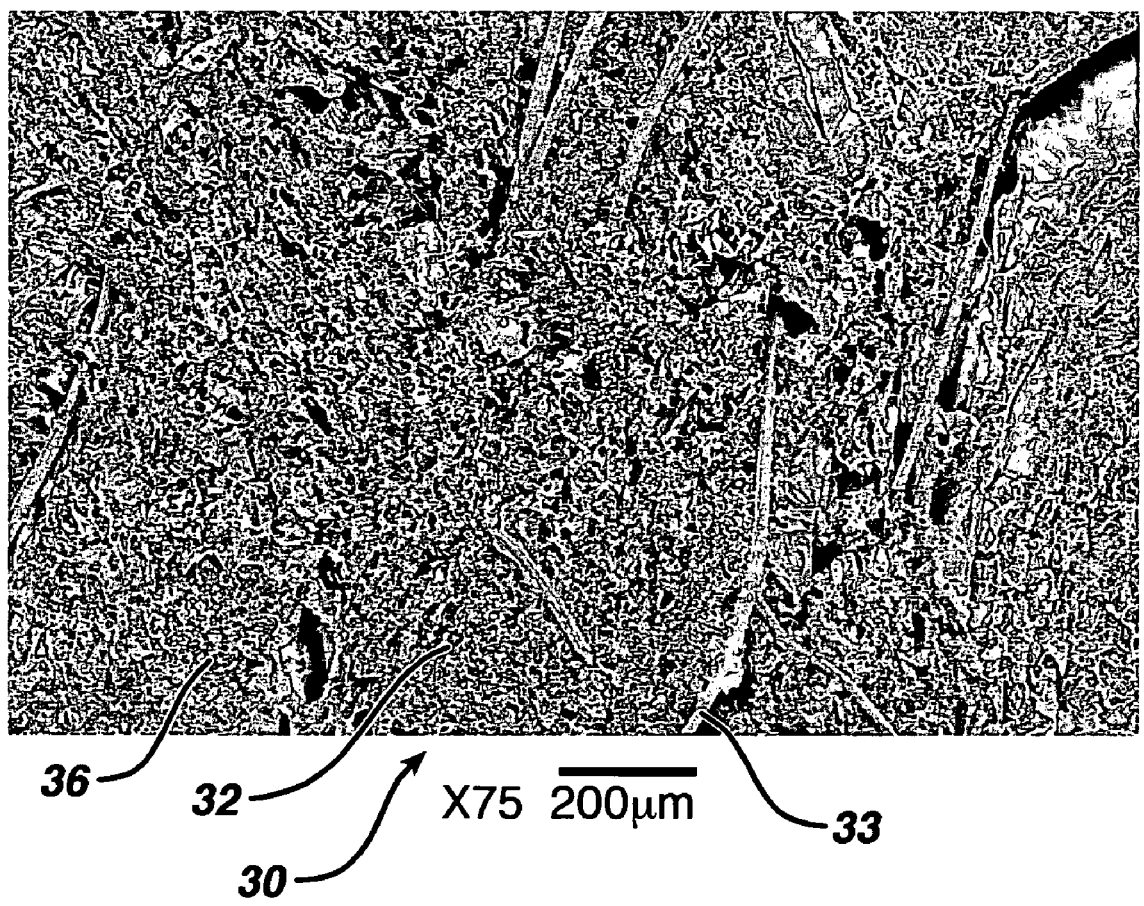
FIG. 8 is a scanning electron microscopy image (×75) of the first surface of a wound dressing of the present invention.
Figure 9:
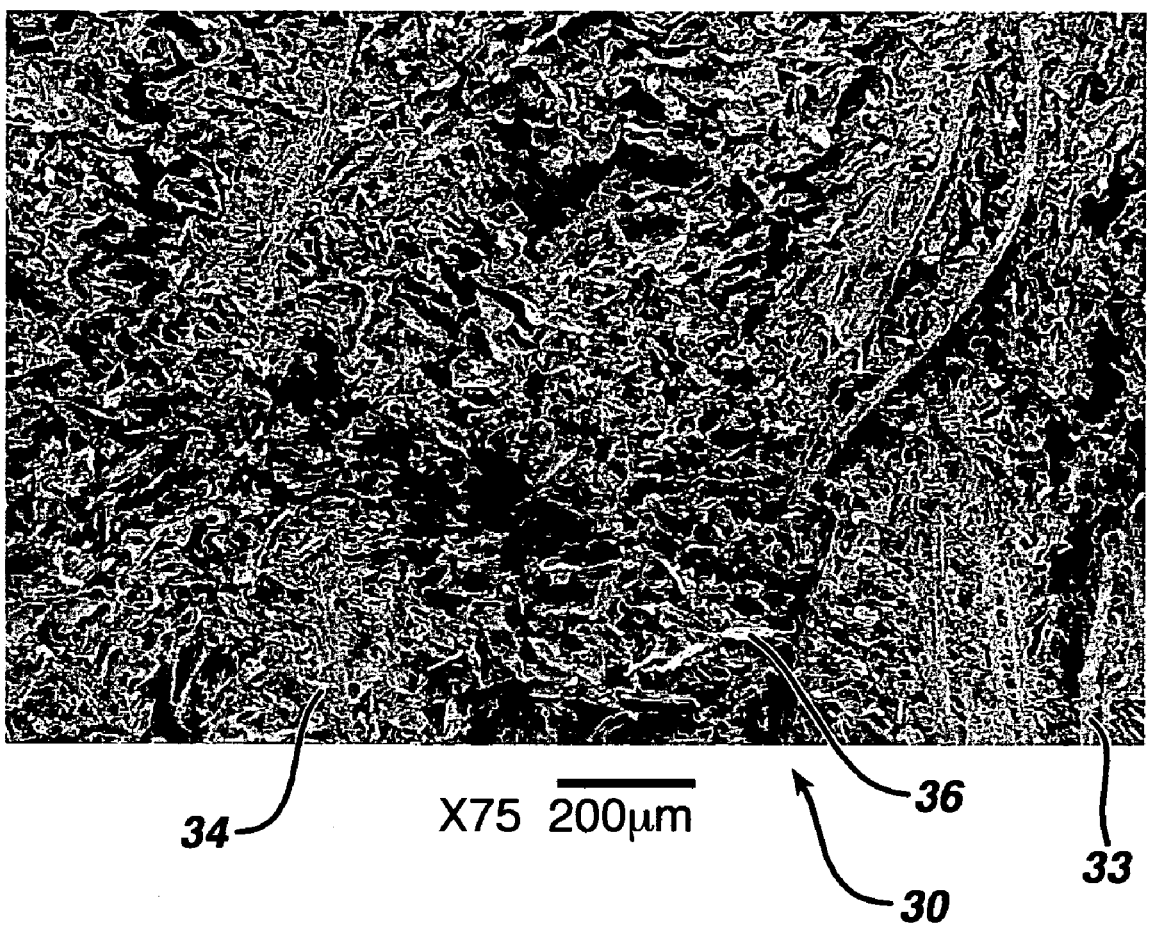
FIG. 9 is a scanning electron microscopy image (×75) of the second opposing surface of a wound dressing of the present invention.

As shown in FIGS. 8 and 9, the matrix disposed on the relative surfaces contains countless pores, ranging from about two microns to as large as about 35 microns in diameter or greater. FIG. 8 shows surface 32 of fabric 30. As noted, polymer 36 is present in the form of a porous matrix about fibers 33, thereby providing ample polymer surface area with which body fluids can interact upon contact therewith. Opposing surface 34 shown in FIG. 9 also contains polymer 36 in the form of a porous matrix about fibers 33.

It is clear from FIGS. 6-9 that fabrics and wound dressings of the present invention contain a porous polymeric matrix dispersed on the surfaces and substantially homogeneously through the fabric. Due to the porous nature of the matrix, body fluids are permitted to pass into the matrix, where ample surface area of polymer is present to interact with the body fluids. This results in faster and a higher degree of hemostasis, particularly where bleeding is occurring at a high volume and rate.

It also is clear from FIGS. 3-5 that comparative fabrics and wound dressings do not contain a porous, polymeric matrix, either on a surface of the dressing or dispersed throughout the fabric. As a result, the amount of polymer present to interact with body fluids is significantly reduced. In addition, due to the formation of agglomerated polymer layers during air drying, body fluids are not permitted to pass freely into the wound dressing where they can interact with and bind to the dressing. Both of these characteristics result in less hemostasis, such that wound dressings of this construct do not provide and maintain hemostasis in cases of severe bleeding. Additionally, such fabrics were found to be brittle and stiff, such that placement within and conformance to a wound site by a physician is not acceptable.

As shown in FIGS. 6 and 7, the polymer matrix disposed on the respective surfaces contains countless pores, ranging from about ten microns to as large as about 400 microns in diameter, or greater. FIG. 6 shows surface 32 of fabric 30. As noted, polymer 36 is present in the form of a porous matrix about fibers 33, thereby providing ample polymer surface area with which body fluids can interact upon contact therewith. Surface 34 shown in FIG. 7 also contains polymer 36 in the form of a porous matrix dispersed about fibers 33, thereby generating a sponge-like polymer matrix structure in concert with the fibers.

It is clear from FIGS. 6-7 that fabrics and wound dressings of the present invention contain a porous polymeric matrix dispersed on the surface and substantially homogeneously through the fabric. Due to the porous nature of the matrix, body fluids are permitted to pass into the matrix, where ample surface area of polymer is present to interact with the body fluids. This results in faster and a higher degree of hemostasis.

Figure 10:
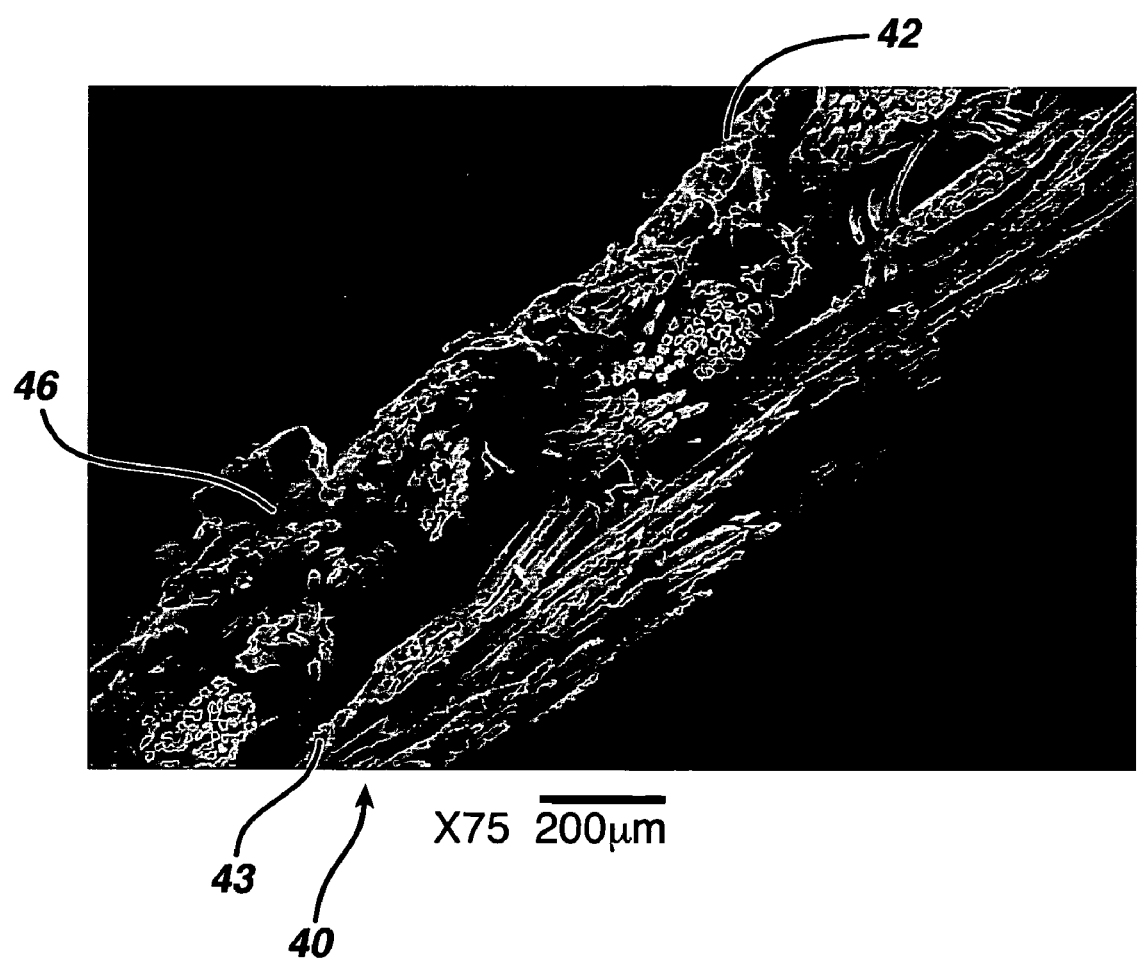
FIG. 10 is a scanning electron microscopy image (×75) of a cross-section of a wound dressing of the present invention.
Figure 11:
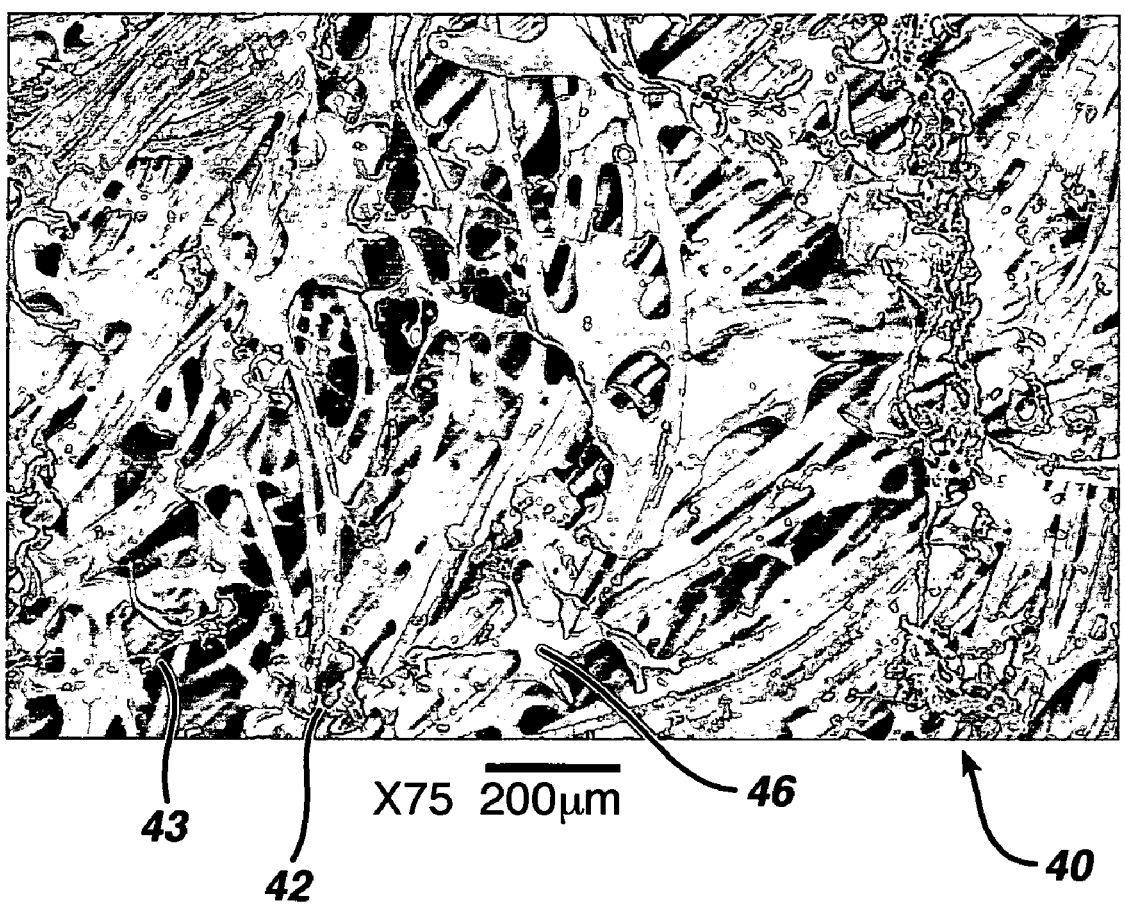
FIG. 11 is a scanning electron microscopy image (×75) of the first surface of a wound dressing of the present invention.
Figure 12:
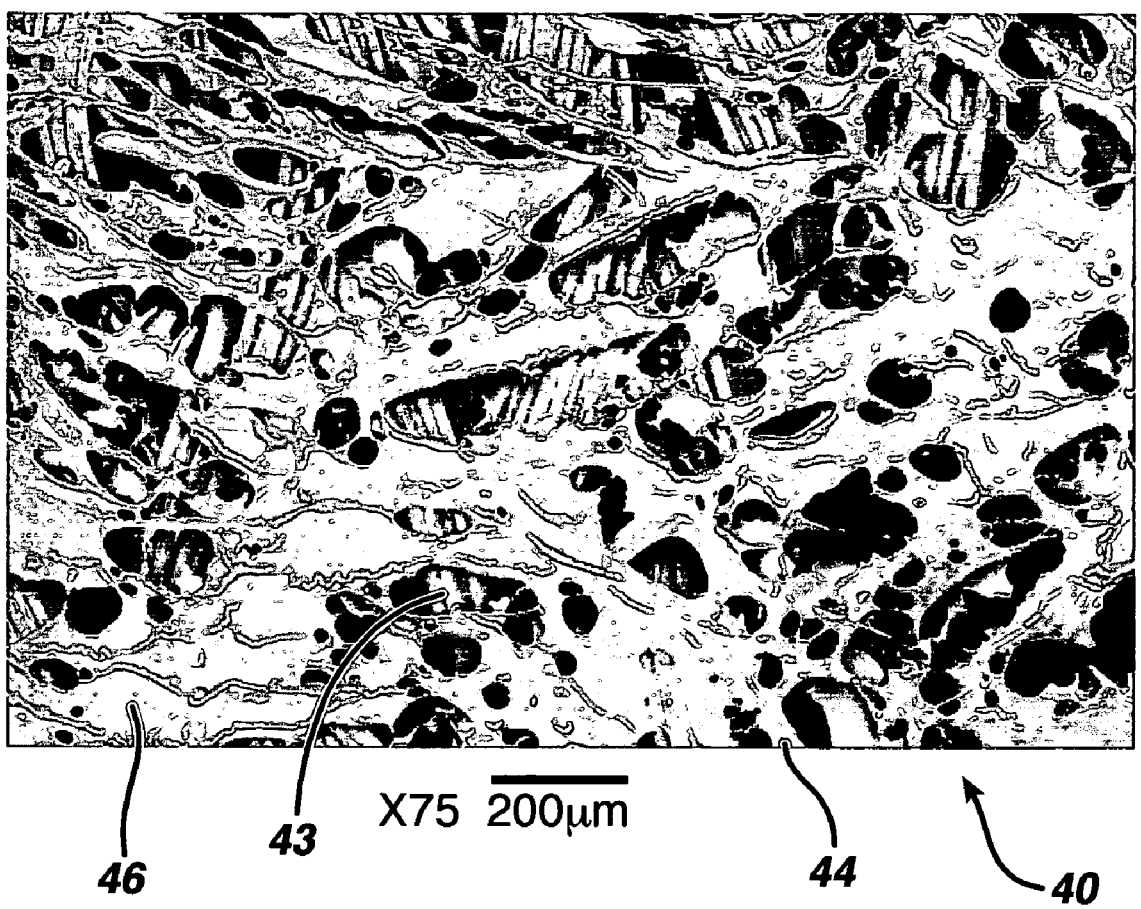
FIG. 12 is a scanning electron microscopy image (×75) of the second opposing surface of a wound dressing of the present invention.

Hemostatic wound dressings fabricated from aldehyde-oxidized regenerated cellulose according to the present invention are represented in FIGS. 10-12.

As shown in FIG. 10, a porous, polymer matrix is substantially uniformly distributed on surface 42 and throughout fabric 40. Polymer 46 forms a porous, polymer matrix integrated with the knitted fibers 43. The porous, polymer matrix exhibits significant liquid absorption properties from capillary action in the same manner as a sponge.

As shown in FIGS. 11 and 12, the polymer matrix disposed on the relative surfaces contains countless pores, ranging from about ten microns to as large as about 400 microns in diameter, or greater. FIG. 11 shows surface 42 of fabric 40. As noted, polymer 46 is present in the form of a porous matrix about fibers 43, thereby providing ample polymer surface area with which body fluids can interact upon contact therewith. Opposing surface 44 shown in FIG. 12 also contains polymer 46 in the form of a porous matrix dispersed about fibers 43, thereby generating a sponge-like polymer matrix structure in concert with the fibers.

It is clear from FIGS. 10-12 that fabrics and wound dressings of the present invention contain a porous, polymeric matrix dispersed on the surfaces and substantially homogeneously through the fabric. Due to the porous nature of the matrix, body fluids are permitted to pass into the matrix, where ample surface area of polymer is present to interact with the body fluids. This results in faster and a higher degree of hemostasis.

As stated above, in order to preserve the porous structure of the polymeric matrix and the homogeneity thereof, it is important to maintain the preferred weight ratio of polymer to fabric during the process of making the wound dressing and the homogenous distribution of the polymer solution on the surface of and throughout the fabric substrate in order to avoid defects on and throughout the wound dressing. In a laboratory setting, this is readily achieved, as the contacting of the fabric substrate with the polymer solution in the laboratory crystallization dish, saturation of the fabric substrate material in the polymer solution and the subsequent lyophilization of the fabric and solution in the dish all take place in the lyophilization unit, where a precise quantity of water-soluble and water-swellable polymer can be used to prepare the solution. No transfer of the saturated fabric or the dish into the lyophilization unit is necessary. As a result, a homogeneous distribution of polymer on fabric is achieved. However, in a manufacturing setting, due to its larger scale, such a process is no longer feasible. A larger container, e.g. a tray or pan, is used instead to hold the fabric and the polymer solution during contacting and saturation of the fabric by the solution, which is conducted outside of the lyophilization unit. The saturated fabric then must be transferred into the lyophilization unit for further processing.

Certain problems are associated with producing a wound dressing of the present invention on a larger scale as described above, where the wound dressing will possess mechanical and hemostatic properties suitable for use as a hemostatic dressing. For instance, if one were to attempt to transfer the container having the polymer solution and saturated fabric disposed therein into the lyophilization unit, during transfer of the container into the lyophilization unit, it is difficult to maintain a constant level of the polymer solution above the fabric in the tray due to movement, e.g. shifting or "sloshing", of the solution in relation to the fabric. In some cases during movement of the container, the fabric surface may even be exposed and the turbulence of the shifting polymer solution in the container may result in poor distribution of polymer on the surface of and through the fabric, particularly with respect to the distribution of the polymer on the surface. This in turn is detrimental to the effectiveness of the hemostatic property of the wound dressing.

In order to maintain the level of solution above the fabric surface prior to lyophilization to ensure that the fabric remains immersed in the polymer solution in order to provide homogeneous distribution on and throughout the fabric, an excess amount of polymer solution must be placed in the container. However, such an approach has not been successful because such an excess amount of polymer solution may result in an undesirable weight ratio of polymer to fabric, which consequently leads to a loss in the flexibility of the wound dressing and of the microporous structure of the polymeric matrix of the hemostatic wound dressing.

To solve this problem, processes of the present invention utilize a transfer support means, e.g. a transfer sheet or carrier, in order to transfer the saturated fabric from the container used to saturate the fabric with polymer solution into the lyophilization unit. However, in order to maintain the homogeneous distribution of the porous, polymeric matrix on and through the fabric substrate after lyophilization, caution must be exercised to minimize disturbance of the homogenous distribution of polymer solution in relationship to the fabric and to minimize deformation, e.g. stretching or tearing, of the fabric substrate during transfer into the lyophilization unit. In addition, the formation of air bubbles or voids between the fabric substrate and the transfer support means while transferring the fabric to the support means must be substantially avoided so as not to create an unacceptable number defects in the wound dressing.

Figure 13:
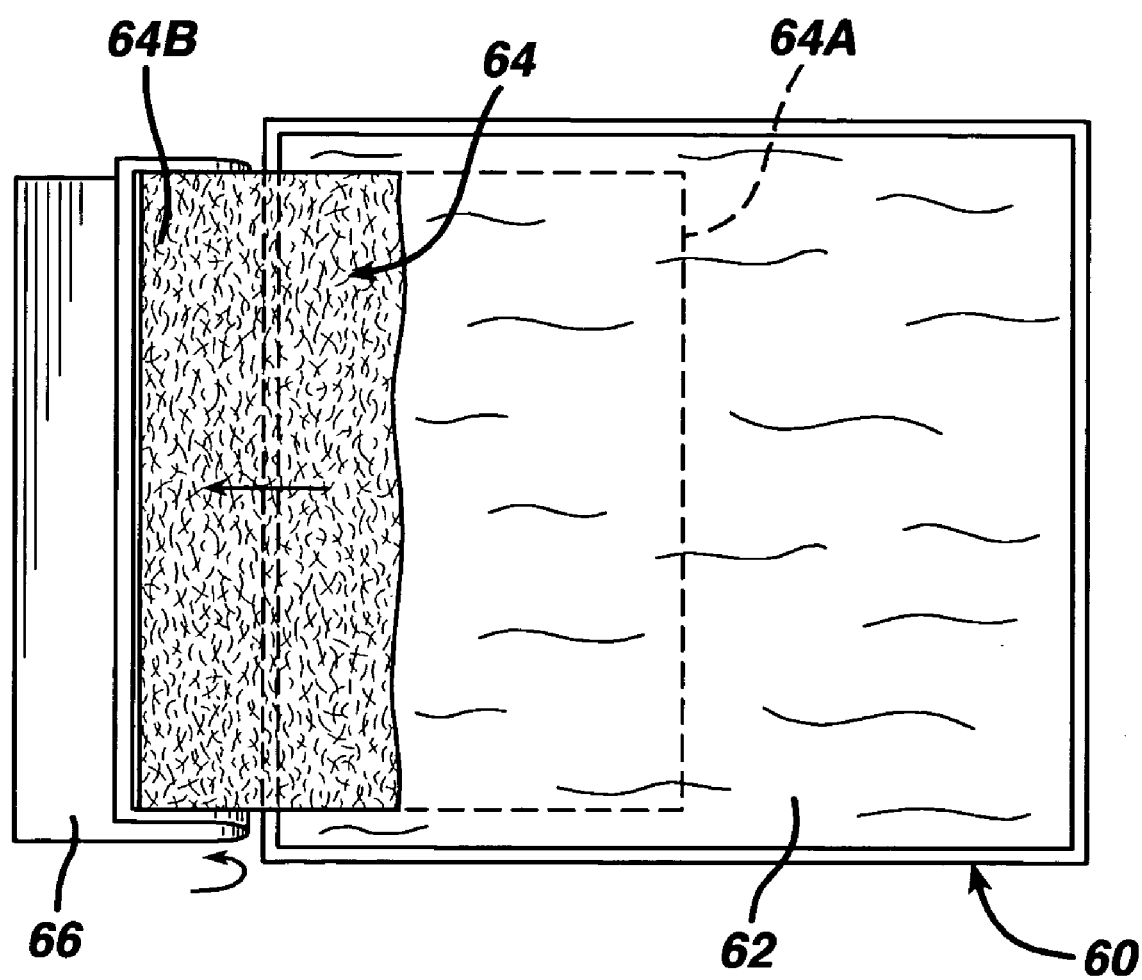
FIG. 13 is a top plan view of the transfer of the saturated fabric from the polymer solution to a transfer support means.
Figure 14:
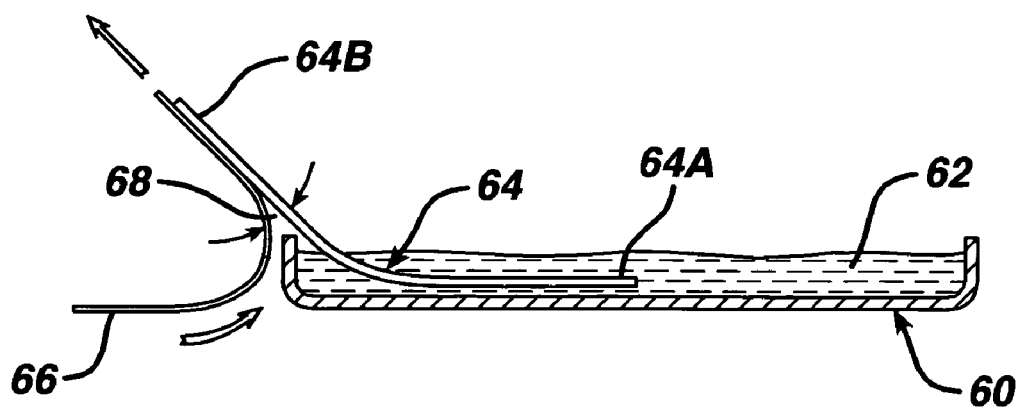
FIG. 14 is an elevational side view of the transfer of the saturated fabric from the polymer solution to a transfer support means.
Figure 15:
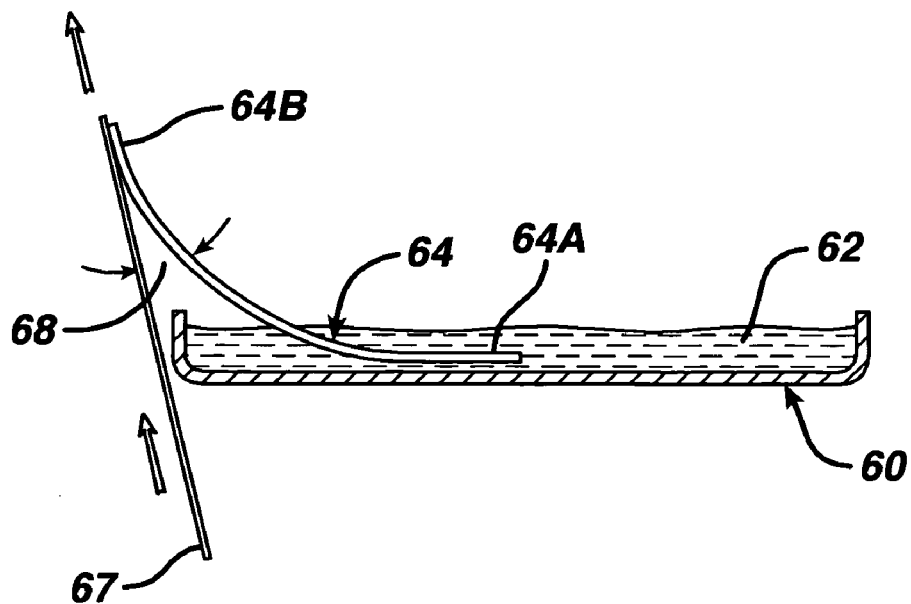
FIG. 15 is an elevational side view of the transfer of the saturated fabric from the polymer solution to a transfer support means.
Figure 17A:
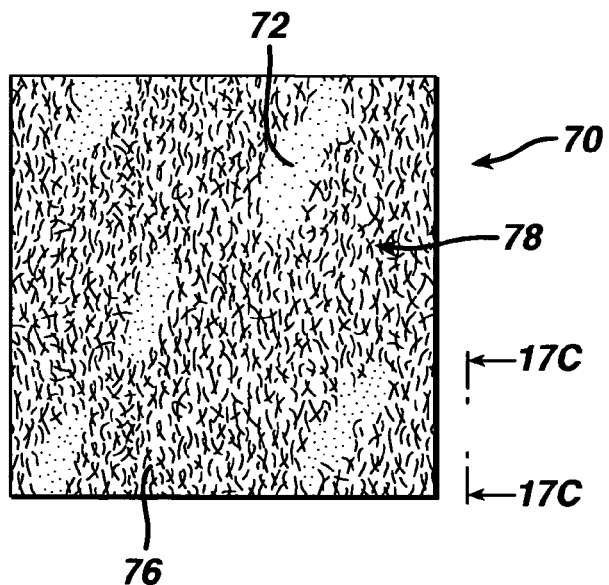
FIG. 17a is a plan view of the first surface of a wound dressing prepared by a comparative method.
Figure 17B:
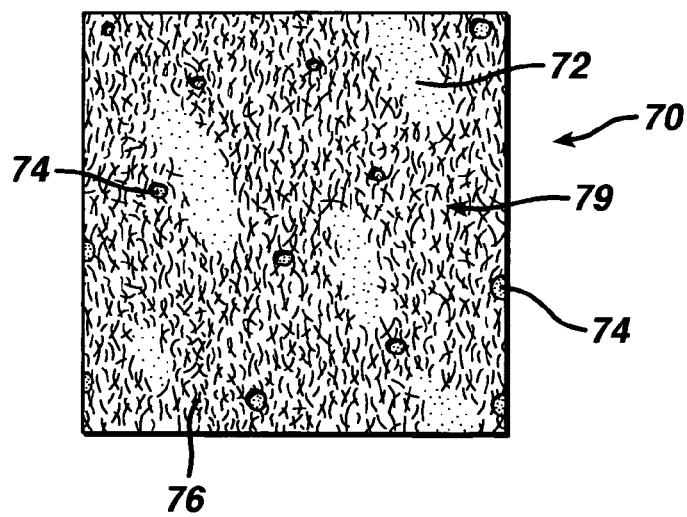
FIG. 17b is a plan view of the second surface of a wound dressing prepared by a comparative method.
Figure 17C:
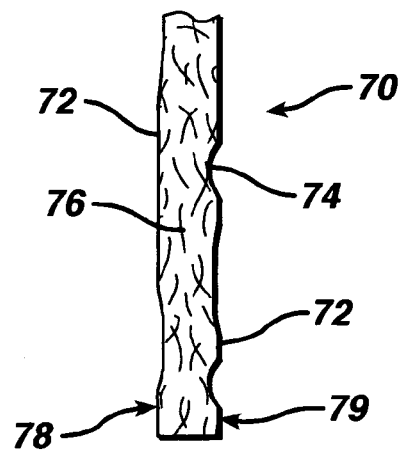
FIG. 17c is enlarged fragmentary side view as seen along view line 17C-17C of a wound dressing prepared by a comparative method.

In accordance with the invention, the method provides for the transfer of the saturated fabric substrate onto the transfer support mean and transferring the saturated fabric substrate and support means to a lyophilization unit. As shown in FIGS. 13-15, where like numbers are used to identify like features, polymer solution 62 is placed in container 60. Fabric 64 then is placed in container 60 and submerged in solution 62 for a period of time sufficient to saturate fabric 64 with solution 62. Saturated fabric substrate 64 is transferred from container 60 onto support means 66 in a manner such that the homogenous distribution of polymer solution on and through the fabric is substantially maintained and that the presence of defects due to air that has been trapped between the fabric and support means is minimized.

The transfer of saturated fabric 64 onto support means 66 is accomplished in a fashion to create a hydraulic pressure sufficient to allow air bubbles to escape from between the fabric substrate and the support means. Distal end 64b of fabric 64 is joined with support means 66 and moved in a continuous fashion as shown, at a controlled rate, while maintaining a desired angle of incidence 68 between fabric 64 and support means 66 until proximal end 64a also is supported by support means 66 to prevent, or at least minimize bubble formation. At the same time, maintaining such conditions of transfer also prevent, or at least minimize, physical deformation of the substrate, such as stretching or tearing. Preferably, the angle of incidence between the fabric and the support means will range from about 20° to about 90°. More preferably, the angle of incidence will range from about 30° to about 60°. Even more preferably, the angle of incidence will be about 45°. The rate of advancing the fabric onto the support means preferably will range from about 8 inches per minute to about 2 inches per minute. Preferably, the rate of transfer is about 7 inches per minute.

The support means should be made of an inert material that will not release any toxic chemical substance or any substance that may alter the characteristics of the wound dressing. It is important that the support means does not alter the freezing and drying parameters associated with the lyophilization process stated above. Therefore, the material used for the support means should be cryolitically stable, such that it may withstand extremely low temperatures without deformation, preferably down to about −50° C. If the support means is not stable at low temperatures, deformation of the means will lead to defects in the wound dressing.

It is important that the support means used for transferring the saturated fabric is of density, mechanical strength, flexibility and thickness to provide sufficient support for the fabric, while avoiding excessive bending and mechanical deformation of the saturated fabric substrate. If the support means is too thick and rigid, it may be difficult to slide the saturated fabric onto the support means. If the supporting means is too soft and flexible, the saturated fabric may bend excessively, thereby causing stretching or other mechanical deformation, which may lead to pooling and running of the polymer solution on the surface, or the creation of surface defects during lyophilization.

It is also important that the support means used for transferring the fabric substrate provides a smooth and flat surface to prevent air bubbles from being trapped under the saturated fabric substrate. The transfer means further must possess heat transfer efficiency suitable for rapid freezing of the fabric/polymer construct and removal of the solvent under high vacuum in the lyophilization unit so as to maintain the homogenous distribution of the porous, polymer matrix on and through the fabric substrate after lyophilization. By heat transfer efficiency, it is meant that heat is transferred quickly from the support means to the saturated fabric to facilitate rapid freezing. A preferred support means is a high-density polyethylene sheet having a preferred thickness of between about 50 mils and about 200 mils. Most preferred support means is high-density polyethylene having a preferred thickness of between about 60 mils and about 100 mils.

Wound dressings that have been prepared according to the inventive process set forth in example 27 are depicted in FIGS. 16a-16c. As shown therein, the distribution of lyophilized polymer on both surface 52 and surface 54 of wound dressing 50 is substantially homogenous. Furthermore, surface 54, contacting the support means, is free of defects caused by entrapped air bubbles.

Wound dressings prepared by comparative processes according to examples 28 and 29 are depicted in FIGS. 17a-17c and 18a-18c. As shown FIGS. 17a-17c, the distribution of lyophilized polymer is not homogenous and excess polymer 72, present as a result of improper transfer of the fabric to the support means, is present throughout both surfaces 78 and 79. Fabric 76 is shown between excess polymer build-up 72. In addition, defects 74 are present, resulting from air bubbles trapped between the support means and surface 79.

Figure 18A:
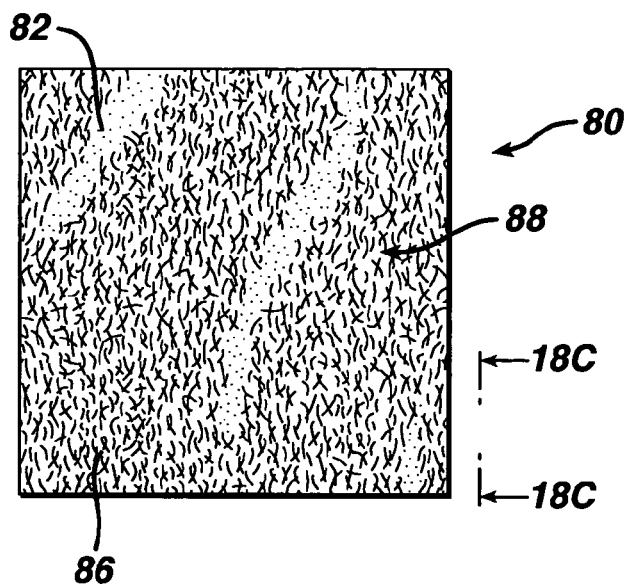
FIG. 18a is plan view of the first surface of a wound dressing prepared by a comparative method.
Figure 18B:
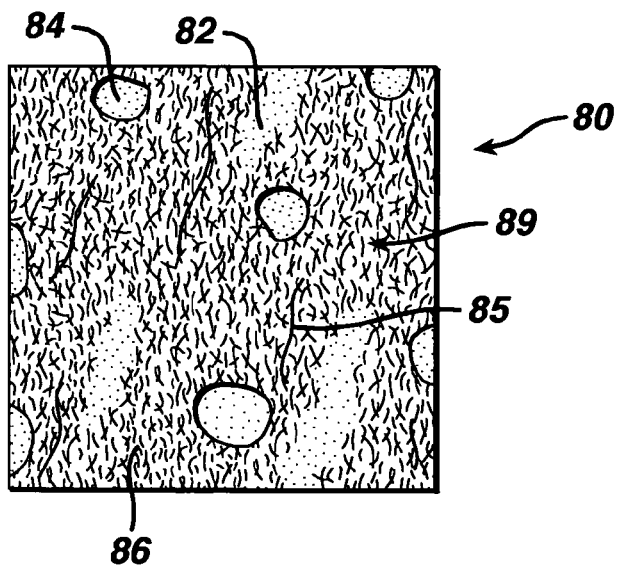
FIG. 18b is a plan view of the second surface of a wound dressing prepared by a comparative method.
Figure 18C:
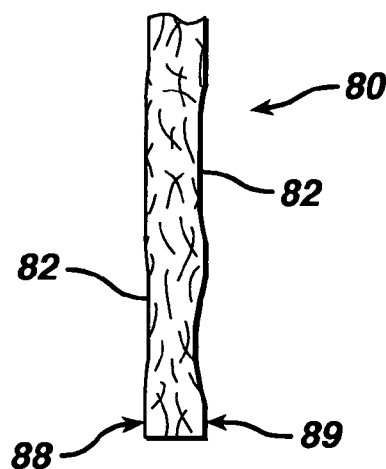
FIG. 18c is an enlarged fragmentary side view as seen along view line 18C-18C of a wound dressing prepared by a comparative method.

Similar results are depicted in FIGS. 18a-18c, where fabric 80 includes excess polymer build-up 82 both on surface 88 and surface 89. Surface 89, having contacted the support means, also includes defects 84 and 85. Defects 85 are due to the support means being too thin and unstable during lyophilization. Fabric 86 is shown between excess polymer build-up 82.

Figure 19A:
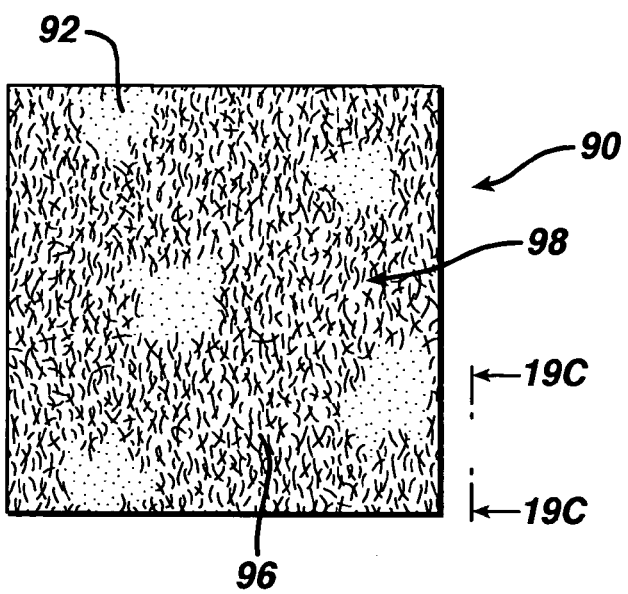
FIG. 19a is a plan view of the first surface of a comparative wound dressing.
Figure 19B:
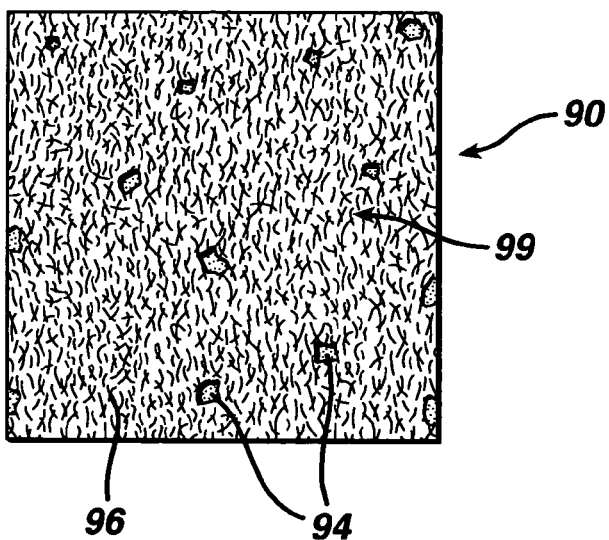
FIG. 19b is a plan view of the first surface of a comparative wound dressing.
Figure 19C:
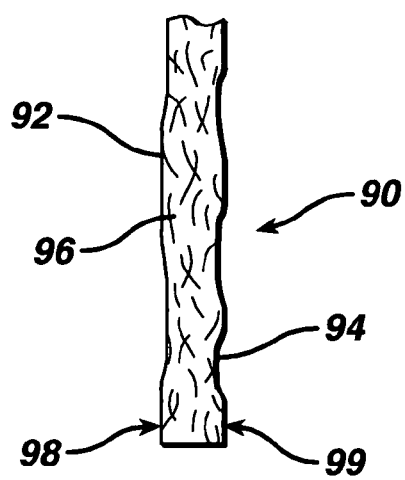
FIG. 19c is an enlarged fragmentary side view as seen along view line 19C-19C view of a comparative wound dressing.

Similar results also are depicted in FIGS. 19a-19c, where fabric 90 includes excess polymer build-up 92 both on surface 98 and surface 99. Surface 99, having contacted the support means, also includes defects 94. Fabric 96 is shown between excess polymer build-up 92.

Figure 20:
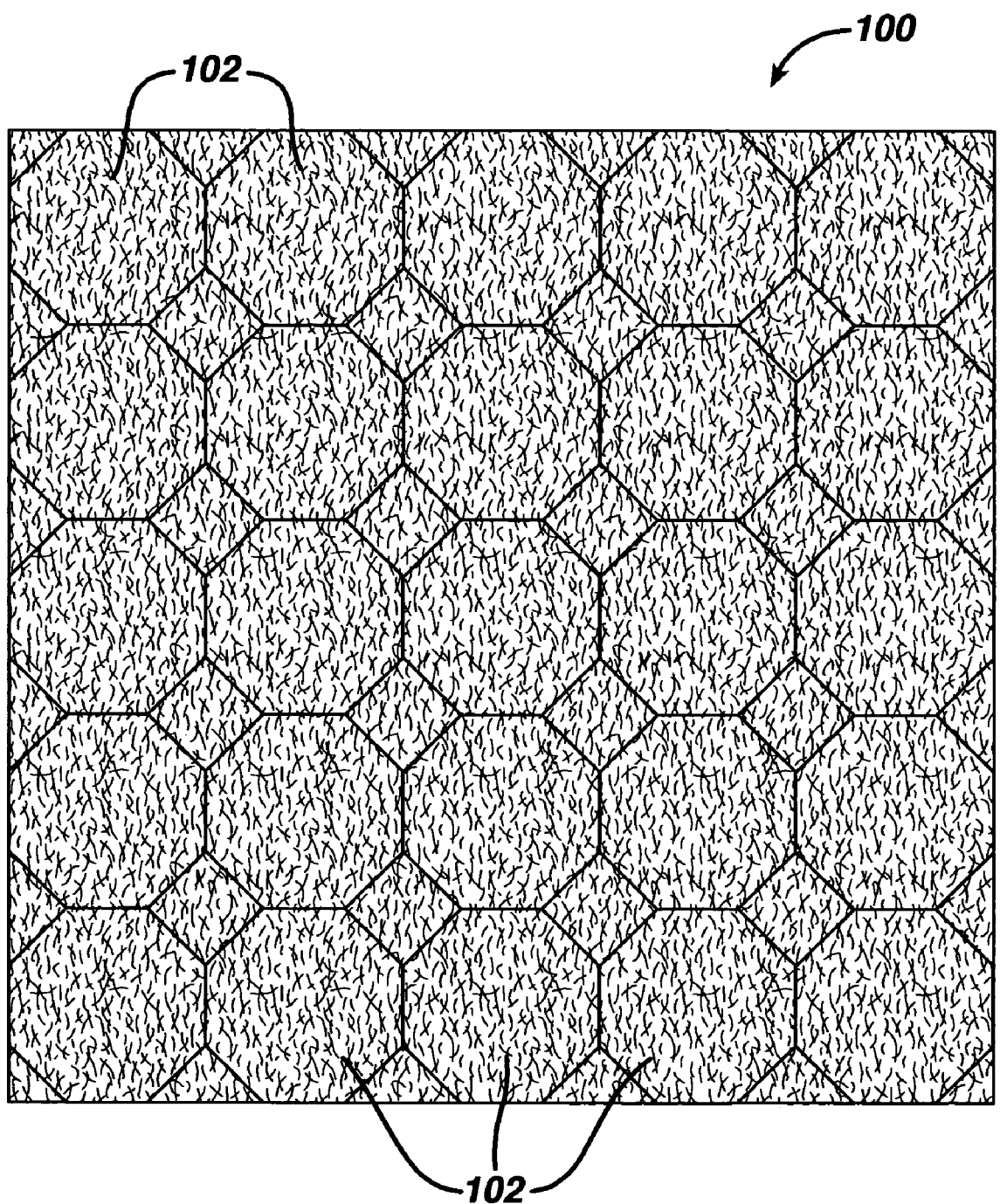
FIG. 20 is a plan view of the surface of a fabric containing wound dressings of the present invention.
Figure 21:
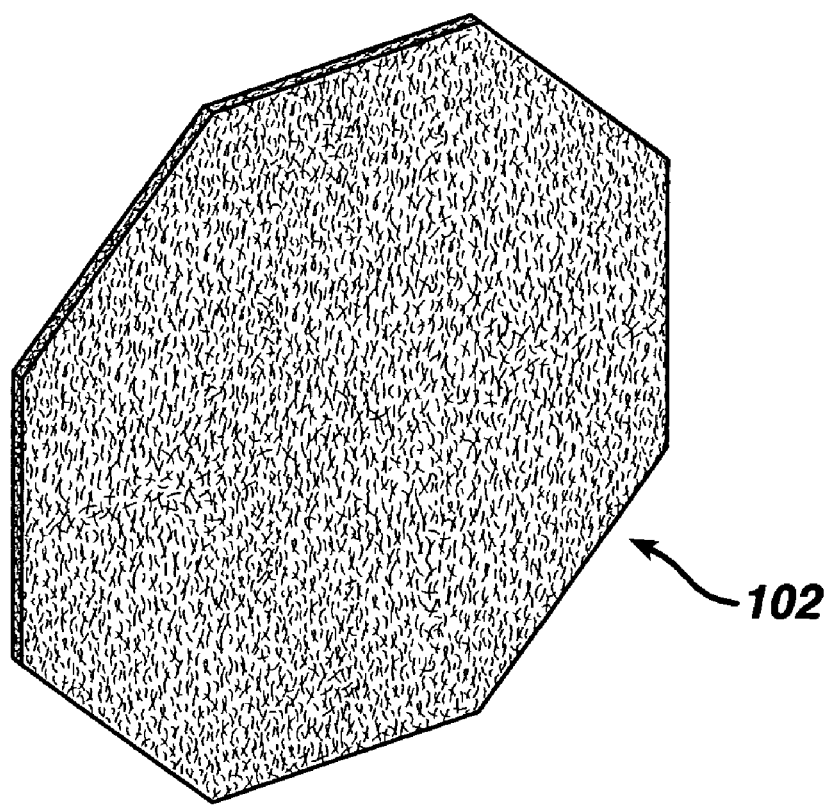
FIG. 21 is a perspective view of a discrete element of a wound dressing of the present invention as shown in FIG. 20.

Once the fabric substrate has the polymeric matrix formed, individual wound dressing patches may be formed from the substrate into any desired shaped. As shown in FIG. 20, several individual patches 92 may be formed, for instance, into an octagonal shape from the fabric substrate. Wound dressing 100 is shown in FIG. 21. Any shape that is suitable for use as a wound dressing may be utilized, as one skilled in the art will readily ascertain from the description. The individual dressing may be formed by, for instance, die cutting, laser cutting, or any method that does not detrimentally affect the hemostatic properties of the dressing.

While the following examples demonstrate certain embodiments of the invention, they are not to be interpreted as limiting the scope of the invention, but rather as contributing to a complete description of the invention.

EXAMPLE 1

Carboxylic-Oxidized Regenerated Cellulose (CORC)/HEC Porous Patch Preparation

One gram of hydroxyethyl cellulose (HEC, from Aldrich) was dissolved in 99 grams of deionized water. After complete dissolution of the polymer, 10 grams of the HEC solution was transferred into a crystallization dish with a diameter of 10 cm. A piece of Surgicel Nu-Knit® absorbable hemostat, based on CORC, having a diameter of 9.8 cm (about 1.3 gram) was placed on the HEC solution in the crystallization dish. After soaking the fabric in the solution for 3 minutes, the wet fabric in the dish was then lyophilized overnight. A very flexible patch was formed. The patch was further dried at room temperature under vacuum.

EXAMPLE 2

CORC/CS Porous Patch Preparation

One gram of cellulose sulfate (CS, from ACROS Organics) was dissolved in 99 grams of deionized water. After complete dissolution of the polymer, 10 grams of the CS solution was transferred into a crystallization dish with a diameter of 10 cm. A piece of Surgicel Nu-Knit® absorbable hemostat with a diameter of 9.8 cm (about 1.3 gram) was placed on the CS solution in the crystallization dish. After soaking the fabric for 3 minutes, the wet fabric was then lyophilized overnight. A very flexible patch was formed. The patch was further dried at room temperature under vacuum.

EXAMPLE 3

CORC/MC Porous Patch Preparation

One gram of methyl cellulose (MC, from Aldrich) was dissolved in 99 grams of deionized water. After complete dissolution of the polymer, 10 grams of the MC solution was transferred into a crystallization dish with a diameter of 10 cm. A piece of Surgicel Nu-Knit® absorbable hemostat with a diameter of 9.8 cm (about 1.3 gram) was placed on the MC solution in the crystallization dish. After soaking the fabric for 3 minutes, the wet fabric in the dish was then lyophilized overnight. A very flexible patch was formed. The patch was further dried at room temperature under vacuum.

EXAMPLE 4

CORC/Water-Soluble Chitosan (WS—CH) Porous Patch Preparation

One gram of WS—CH was dissolved in 99 grams of deionized water. After complete dissolution of the polymer, 10 grams of the WS—CH solution was transferred into a crystallization dish with a diameter of 10 cm. A piece of Surgicel Nu-Knit® absorbable hemostat with a diameter of 9.8 cm (about 1.3 gram) was placed on WS—CH solution in the crystallization dish. After soaking the fabric for 3 minutes, the wet fabric in the dish was then lyophilized overnight. A very flexible patch was formed. The patch was further dried at room temperature under vacuum.

EXAMPLE 5

CORC/Na—CMC Porous Patch Preparation

One gram of sodium salt of CMC (Na—CMC, from Aqualon) was dissolved in 99 grams of deionized water. After complete dissolution of the polymer, 10 grams of the Na—CMC solution was transferred into a crystallization dish with a diameter of 10 cm. A piece of Surgicel Nu-Knit® absorbable hemostat with a diameter of 9.8 cm (about 1.3 gram) was placed on the CMC solution in the crystallization dish. After soaking the fabric for 3 minutes, the wet fabric in the dish was then lyophilized overnight. A very flexible patch was formed. The patch was further dried at room temperature under vacuum.

COMPARATIVE EXAMPLE 6

CORC/Na—CMC Film Preparation

One gram of sodium salt of CMC (Na—CMC, from Aqualon) was dissolved in 99 grams of deionized water. After complete dissolution of the polymer, 10 grams of the Na—CMC solution was transferred into a crystallization dish with a diameter of 10 cm. A piece of Surgicel Nu-Knit® absorbable hemostat with a diameter of 9.8 cm (about 1.3 gram) was placed on the Na—CMC solution in the crystallization dish. The wet fabric in the dish was then air-dried overnight. A rigid and brittle patch was formed. The CORC/Na—CMC film was further dried at room temperature under vacuum. The film was not effective as a hemostat because it was too stiff and did not conform to the bleeding site well.

EXAMPLE 7

Na—CMC Porous Patch Preparation

One gram of sodium salt of CMC (Na—CMC, medium viscosity grade from Sigma) was dissolved in 99 grams of deionized water. After complete dissolution of the polymer, 60 grams of the Na—CMC solution was transferred into a crystallization dish with a diameter of 10 cm. The solution in the dish was then lyophilized overnight. A porous sponge was formed. The patch was further dried at room temperature under vacuum.

EXAMPLE 8

Hemostatic Performance of Different Materials in Porcine Splenic Incision Model

A porcine spleen incision model was used for hemostasis evaluation of different materials. The materials were cut into 2.5 cm×1.5 cm rectangles. A linear incision of 1.5 cm with a depth of 0.3 cm was made with a surgical blade on a porcine spleen. After application of the test article, digital tamponade was applied to the incision for 2 minutes. The hemostasis was then evaluated. Additional applications of digital tamponade for 30 seconds each time were used until complete hemostasis was achieved. Fabrics failing to provide hemostasis within 12 minutes were considered to be failures. Table 1 lists the results of the evaluation.

TABLE 1

Hemostatic performance of different materials

| Material | Percent of test samples to achieve hemostasis within the time period | | | | | |
|---|---|---|---|---|---|---|
| | 0-2 (min) | 2-3 (min) | 3-4 (min) | 4-5 (min) | 5-6 (min) | <12 (min) |
| Surgicel Nu-Knit ® | 0% | 0% | 100% | | | |
| Example 1 patch | 100% | | | | | |
| Example 2 patch | 100% | | | | | |
| Example 3 patch | 100% | | | | | |
| Example 4 patch | 100% | | | | | |
| Example 5 patch | 100% | | | | | |
| Example 6 film | | | 50% | | 50% | |
| Example 7 sponge | | | | | | 0 |
| Surgical gauze | | | | | | 0 |

As indicated from the results, wound dressings prepared using lyophilization as the means for removing solvent improved hemostatic property of hemostatic fabrics, while the air-dried process failed to enhance the hemostatic property of hemostatic fabrics. Additionally, lyophilized Na—CMC sponge alone failed to achieve hemostasis.

EXAMPLE 9

Hemostatic Performance of Example 5 (CORC/Na—CMC) in a Porcine Splenic Arterial Needle Puncture Model A puncture defect was made on a porcine splenic artery with an 18-gauge needle. After the needle was removed, severe bleeding was observed. A test article (2.5 cm×2.5 cm) was applied over the puncture site. Digital pressure was applied over the test article for 2 minutes. The hemostatic performance was evaluated. The observations are listed in Table 2.

TABLE 2

Comparison of Initial time to Hemostasis and Ability of Maintaining Hemostasis

| Material | # of Digital Pressure | Initial Time to Hemostasis | Maintenance of Hemostasis |
|---|---|---|---|
| Surgicel Nu-Knit ® | 1 | <2 min | Re-bleeding occurred after 4 min |
| Example 5 Patch | 1 | <2 min | No Re-bleeding occurred |

EXAMPLE 10

Hemostatic Performance of Different Materials in a Porcine Splenic Incision Model with Tamponade for 30 Seconds A porcine spleen incision model was used for hemostasis evaluation of different materials. The materials were cut into 2.5 cm×1.5 cm rectangles. A linear incision of 1.5 cm with a depth of 0.3 cm was made with a surgical blade on porcine spleen. After application of the test article, digital tamponade was applied to the incision for 30 seconds. The hemostasis evaluation was then performed. Additional applications of digital tamponade for 30 seconds each time were used until complete hemostasis was achieved. Table 3 lists the results of the evaluation.

TABLE 3

Hemostatic performance of different materials in a splenic incision model

| Material | # of Digital Pressure | Time to Hemostasis |
|---|---|---|
| Surgicel Nu-Knit ® | 5 | 2 min 55 sec |
| Example 5 Patch | 1 | <30 sec |

EXAMPLE 11

Hemostatic Performance of Different Materials in a Porcine Splenic Cross-Hatch Model A porcine spleen cross-hatch model was used for hemostasis evaluation of different materials. The materials were cut into 3 cm×3 cm squares. A surgical defect (2 cm×2 cm, 0.2 cm deep) was made with a surgical blade on the porcine spleen. Additional bleeding was induced by making three additional equally spaced, side-to-side horizontal incisions and three additional equally spaced, side-to-side vertical incisions within the defect. After application of the test article, digital tamponade was applied to the incision for 2 minutes. The hemostasis evaluation was then performed. Additional applications of digital pressure for 30 second each time were used until complete hemostasis was achieved. Table 4 lists the results of the evaluation.

TABLE 4

Hemostatic performance of different materials in a splenic cross-hatch model

| Material | # of Digital Pressure | Time to Hemostasis |
|---|---|---|
| Surgicel Nu-Knit ® | 4 | 3 min 55 sec |
| Example 5 Patch | 1 | <2 min |

EXAMPLE 12

Preparation of Knitted Aldehyde-Oxidized Regenerated (AORC) Cellulose Fabric

A 15.8 g piece of knitted rayon fabric as described herein was cut in the form of a strip 1.5 inches wide. The strip was wound on a mandrel and suspended in 600 ml of aqueous isopropyl alcohol (IPA) (200 ml IPA/400 ml de-ionized (DI) water). 20.8 g of sodium periodate (Aldrich, Milwaukee, 53201) was dissolved in the solution (1:1 molar ratio) and the mandrel was rotated at moderate rpm in the solution for 21 hours at ambient temperature. It is essential that the oxidation of the fabric be conducted in the dark. The solution pH was 3.8. The solution was discarded after the reaction. The mandrel with the oxidized fabric was washed for 30 minutes in 1 liter of cold DI water containing 50 ml of ethylene glycol. It was then washed with aqueous IPA (50/50) for 15 minutes, followed by a pure IPA wash for 15 minutes. The fabric was dried in ambient air for several hours.

The oxidized fabric then was evaluated for hemostasis as set forth below. Results are provided in Table 5.

EXAMPLE 13

Preparation of Water-Soluble Aldehyde-Oxidized Methylcellulose (AOMC)

100 g of a 5% methylcellulose (MC, Ave. Mn 63 kD, lot# 06827ES from Aldrich, Milwaukee, Wis.) aqueous solution was combined with 3 g of periodic acid (Aldrich, Milwaukee, 53201) and was then stirred for 5 hours at ambient temperature in the dark. 1.5 ml of ethylene glycol was added to the reaction solution and stirred for 30 minutes. 2000 ml of acetone were added slowly into the reaction solution to precipitate the AOMC. The reaction mixture was allowed to stand for 20-30 minutes to separate the liquid phase from the solid phase. The supernatant then was removed and the solid phase centrifuged to precipitate the solids. The solid precipitate was dissolved in 100 ml DI over night followed by dialysis for 72 hours. The final wet mixture was lyophilized to form a sponge/foam.

EXAMPLE 14

Preparation of Water-Soluble Aldehyde-Oxidized Hydroxyethyl Cellulose (AOHC)

100 g of a 5% hydroxyethyl cellulose (HEC, Ave. Mv; 720 kD lot # 02808DU from Aldrich, Milwaukee, Wis.) aqueous solution was combined with 3 g of periodic acid (Aldrich, Milwaukee, 53201) and was then stirred for 5 hours at ambient temperature in the dark. 1.5 ml of ethylene glycol was added to the reaction solution and stirred for 30 minutes. 2000 ml of acetone were added slowly into the reaction solution to precipitate the AOHC. The reaction mixture was allowed to stand for 20-30 minutes to separate the liquid phase from the solid phase. The supernatant then was removed and the solid phase centrifuged to precipitate the solids. The solid precipitate was dissolved in 100 ml DI over night followed by dialysis for 72 hours. The final wet mixture was lyophilized to form a sponge/foam.

EXAMPLE 15

AORC/HEC Porous Patch Preparation

One gram of hydroxyethyl cellulose (HEC, Lot # GI01 from TCI, Tokyo, Japan) was dissolved in 99 grams of deionized water. After complete dissolution of the polymer, 10 grams of the HEC solution was transferred into a crystallization dish with a diameter of 10 cm. A piece of AORC fabric (about 1.3 gram) was placed on the HEC solution in the crystallization dish. After soaking the fabric in the solution for 3 minutes, the wet fabric in the dish was lyophilized overnight. A very flexible patch was formed. The patch was further dried at room temperature under vacuum. The AORC/HEC patch then was evaluated for hemostasis as set forth below. Results are provided in Table 5.

EXAMPLE 16

AORC/CS Porous Patch Preparation

One gram of cellulose sulfate (CS, lot # A013801301 from ACROS Organics, New Jersey) was dissolved in 99 grams of deionized water. After complete dissolution of the polymer, 10 grams of the CS solution was transferred into a crystallization dish with a diameter of 10 cm. A piece of AORC fabric (about 1.3 gram) was placed on the CS solution in the crystallization dish. After soaking the fabric for 3 minutes, the wet fabric was lyophilized overnight. A very flexible patch was formed. The patch was further dried at room temperature under vacuum.

The AORC/CS patch then was evaluated for hemostasis as set forth below. Results are provided in Table 5.

EXAMPLE 17

AORC/MC Porous Patch Preparation

One gram of methyl cellulose (MC, Ave. Mn 63 kD, lot# 06827ES from Aldrich, Milwaukee, Wis.) was dissolved in 99 grams of deionized water. After complete dissolution of the polymer, 10 grams of the MC solution was transferred into a crystallization dish with a diameter of 10 cm. A piece of AORC fabric (about 1.3 gram) was-placed on the MC solution in the crystallization dish. After soaking the fabric for 3 minutes, the wet fabric in the dish was lyophilized overnight. A very flexible patch was formed. The patch was further dried at room temperature under vacuum.

The AORC/MC patch then was evaluated for hemostasis as set forth below. Results are provided in Table 5.

EXAMPLE 18

AORC/CMC—Na Porous Patch Preparation

One gram of sodium salt of carboxymethyl cellulose (CMC—Na, Type 7M8SF Lot#: 77521 from Aqualon, Wlmington, Del.) was dissolved in 99 grams of deionized water. After complete dissolution of the polymer, 10 grams of the Na—CMC solution was transferred into a crystallization dish with a diameter of 10 cm. A piece of AORC fabric (about 1.3 gram) was placed on the CMC solution in the crystallization dish. After soaking the fabric for 3 minutes, the wet fabric in the dish was lyophilized overnight. A very flexible patch was formed. The patch was further dried at room temperature under vacuum.

The AORC/CMC—Na patch then was evaluated for hemostasis as set forth below. Results are provided in Table 5.

EXAMPLE 19

AORC/CMC—Na Porous Patch Preparation

One gram of sodium salt of carboxymethyl cellulose (CMC—Na, Type: 7H4F Lot#: 79673 from Aqualon, Wilmington, Del.) was dissolved in 99 grams of deionized water. After complete dissolution of the polymer, 10 grams of the Na—CMC solution was transferred into a crystallization dish with a diameter of 10 cm. A piece of AORC fabric (about 1.3 gram) was placed on the CMC solution in the crystallization dish. After soaking the fabric for 3 minutes, the wet fabric in the dish was then lyophilized overnight. A very flexible patch was formed. The patch was further dried at room temperature under vacuum.

The AORC/CMC—Na patch then was evaluated for hemostasis as set forth below. Results are provided in Table 5.

EXAMPLE 20

AORC/HEC Porous Patch Preparation

One gram of hydroxyethyl cellulose (HEC, Ave. Mv; 720 kD lot # 02808DU from Aldrich, Milwaukee, Wis.) was dissolved in 99 grams of deionized water. After complete dissolution of the polymer, 10 grams of the HEC solution was transferred into a crystallization dish with a diameter of 10 cm. A piece of AORC fabric (about 1.3 gram) was placed on the HEC solution in the crystallization dish. After soaking the fabric in the solution for 3 minutes, the wet fabric in the dish was lyophilized overnight. A very flexible patch was formed. The patch was further dried at room temperature under vacuum.

The AORC/HEC patch then was evaluated for hemostasis as set forth below. Results are provided in Table 5.

EXAMPLE 21

AORC/HEC/Thrombin Porous Patch Preparation

One gram of hydroxyethyl cellulose (HEC, Ave. Mv; 720 kD lot # 02808DU from Aldrich, Milwaukee, Wis.) was dissolved in 99 grams of deionized water. After complete dissolution of the polymer, 20 ml of the MC solution was used to reconstitute thrombin in a vial (20,000 units). 2.5 ml of the cloudy solution was transferred into a crystallization dish. A piece of AORC fabric (about 1 gram) was placed on the HEC solution in the crystallization dish. After soaking the fabric in the solution for 3 minutes, the wet fabric in the dish was lyophilized overnight. A very flexible patch was formed. The patch was further dried at room temperature under vacuum.

The AORC/HEC/Thrombin porous patch then was evaluated for hemostasis as set forth below. Results are provided in Table 5.

EXAMPLE 22

AORC/MC/Thrombin Porous Patch Preparation

One gram of methyl cellulose (MC, Ave. Mn 63 kD, lot# 06827ES from Aldrich) was dissolved in 99 grams of deionized water. After complete dissolution of the polymer, 20 ml of the MC solution was used to reconstitute thrombin in a vial (20,000 units). 2.5 ml of the cloudy solution was transferred into a crystallization dish. A piece of AORC fabric (about 1 gram) was placed on the MC solution in the crystallization dish. After soaking the fabric in the solution for 3 minutes, the wet fabric in the dish was lyophilized overnight. A very flexible patch was formed. The patch was further dried at room temperature under vacuum.

The AORC/MC/Thrombin porous patch then was evaluated for hemostasis as set forth below. Results are provided in Table 5.

EXAMPLE 23

AORC/AOMC/Thrombin Porous Patch Preparation

One gram of AOMC from Example 13 was dissolved in 99 grams of deionized water. After complete dissolution of the polymer, 20 ml of the AOMC solution was used to reconstitute thrombin in a vial (20,000 units). 2.5 ml of the cloudy solution was transferred into a crystallization dish. A piece of AORC fabric (about 1 gram) was placed on the AOMC solution in the crystallization dish. After soaking the fabric in the solution for 3 minutes, the wet fabric in the dish was lyophilized overnight. A very flexible patch was formed. The patch was further dried at room temperature under vacuum.

EXAMPLE 24

AORC/AOHEC/Thrombin Porous Patch Preparation

One gram of AOHEC(MW=90 kD, from Aldrich) synthesized as per example 3 was dissolved in 99 grams of deionized water. After complete dissolution of the polymer, 20 ml of the AOHEC solution was used to reconstitute thrombin in a vial (20,000 units). 2.5 ml of the cloudy solution was transferred into a crystallization dish. A piece of AORC fabric (about 1 gram) was placed on the AOHEC solution in the crystallization dish. After soaking the fabric in the solution for 3 minutes, the wet fabric in the dish was lyophilized overnight. A very flexible patch was formed.

The patch was further dried at room temperature under vacuum.

The AORC/AOHEC/Thrombin porous patch then was evaluated for hemostasis as set forth below. Results are provided in Table 5.

EXAMPLE 25

Hemostatic Performance of Different Materials in Porcine Splenic Incision Model A porcine spleen incision model was used for hemostasis evaluation of different materials. The materials were cut into 2.5 cm×1.5 cm rectangles. A linear incision of 1.5 cm with a depth of 0.3 cm was made with a surgical blade on a porcine spleen. After application of the test article, digital tamponade was applied to the incision for 2 minutes. The hemostasis was then evaluated. Additional applications of digital tamponade for 30 seconds each time were used until complete hemostasis was achieved. Fabrics failing to provide hemostasis within 12 minutes were considered to be failures. Table 5 lists the results of the evaluation.

EXAMPLE 26

Hemostatic Performance of Different Materials in a Porcine Splenic Incision Model With Tamponade for 30 Seconds A porcine spleen incision model was used for hemostasis evaluation of different materials. The materials were cut into 2.5 cm×1.5 cm rectangles. A linear incision of 1.5 cm with a depth of 0.3 cm was made with a surgical blade on porcine spleen. After application of the test article, digital tamponade was applied to the incision for 30 seconds. The hemostasis evaluation was then performed. Additional applications of digital tamponade for 30 seconds each time were used until complete hemostasis was achieved. Table 5 lists the results of the evaluation.

TABLE 5

Hemostatic performance of AORC-Based Materials

| Sample | 2 min tamponade Time to Hemostasis (Seconds) | 30 second tamponade Time to Hemostasis (Seconds) |
|---|---|---|
| Example 12 | 187 (n = 11) | |
| Example 15 | 370 (n = 2) | |
| Example 16 | 308 (n = 2) | |
| Example 17 | 285 (n = 1) | |
| Example 18 | 582 (n = 2) | |
| Example 19 | 120 (n = 3) | 230 (n = 2) |
| Example 20 | 187 (n = 3) | 253 (n = 2) |
| Example 21 | | 73 (n = 3) |
| Example 22 | | 30 (n = 3) |
| Example 24 | | 47 (n = 3) |
| Surgical gauze Negative Control | >720 | >720 |

As indicated from the results, wound dressings of the present invention achieve effective hemostasis. In particular, when higher molecular weight water-soluble polymers (CMC—Na and HEC) were used, the corresponding patches achieved better time to hemostasis. Also as indicated from the results, wound dressings of the present invention having hemostatic agents, e.g. thrombin, bound there to achieve even faster time to hemostasis.

EXAMPLE 27

Preparation of CORC/Na—CMC Wound Dressing According to Present Invention 410 grams of sodium salt of CMC (Na—CMC, from Aqualon) was dissolved in 41 liters of sterile water and transferred to a holding tray. A piece of knitted CORC fabric as described herein was cut to 7 in×7 in (about 6 grams) and carefully placed in the Na—CMC solution in the tray, taking care to avoid the entrapment of any air bubbles (Na—CMC solution:knitted CORC fabric ratio is 15:1). The fabric was soaked in the polymer solution for 1-3 minutes. One end of the saturated fabric then was carefully lifted with minimal stretching and placed on a flexible high-density polyethylene support sheet (10 in×14 in×0.0133 in) to join the edges of saturated fabric and support sheet. The adjoined edges were held together and both the support sheet and fabric were forwarded together in a continuous fashion at a constant rate, while maintaining an angle of incidence between the sheet and fabric of about 45 degrees or less to generate a sufficient hydrolic pressure from the saturated fabric to the support sheet to remove any air bubbles that may have become trapped between the saturated fabric and the support sheet. After the saturated fabric was fully transferred onto the support sheet, the support sheet having the saturated fabric disposed thereon was placed on the shelf of a Usifroid (Model No—SMH1575, Serial No—16035) lyphilization unit at a temperature of approximately −50° C. The frozen, saturated fabric on the support sheet then underwent a full lyophilization cycle. A flexible patch with a substantial homogenous distribution of Na—CMC through on and through the fabric was formed. The patch was further dried at 50° C. for 4 hours before packaging.

EXAMPLE 28

Preparation of ORC/Na—CMC Comparative Wound Dressing 410 gram of sodium salt of CMC (Na—CMC, from Aqualon) was dissolved in 41 liters of sterile water and then transferred to a tray. A piece of knitted CORC fabric as described herein was cut into 7 in×7 in (about 6 gram) and carefully placed on the Na—CMC solution in the tray without trapping any air bubbles (Na—CMC solution:knitted CORC fabric ratio is 15:1). The fabric was soaked for 1-3 minutes in order to saturate the fabric with the polymer solution. Immediately upon saturation of the fabric, the saturated fabric was lifted from the container and solution and laid manually onto a flexible high-density polyethylene support sheet of the same type used in Example 27 (10 in×14 in×0.0133). The support sheet having the saturated fabric place thereon then was placed on the shelf of a Usifroid (Model No—SMH1575, Serial No—16035) lyophilization unit at a temperature of approximately −50° C. The frozen, saturated fabric on the support sheet then underwent a full lyophilization cycle. A flexible patch having defects caused by trapped air bubbles and an uneven distribution of Na—CMC on the fabric was formed.

EXAMPLE 29

Preparation of CORC/Na—CMC Comparative Wound Dressing 410 gram of sodium salt of CMC (Na—CMC, from Aqualon) was dissolved in 41 liters of sterile water and then transferred to in tray. A piece of knitted CORC fabric as described herein was cut into 7 in×7 in (about 6 gram) and carefully laid down on the Na—CMC solution in the tray without trapping any air bubbles (Na—CMC solution:knitted CORC fabric ratio is 15:1). The fabric was soaked for 1-3 minutes to allow saturation of the fabric by the polymer solution. Immediately upon saturation of the fabric, the saturated fabric was lifted from the solution and container and transferred manually by hands onto a flexible high-density polyethylene thin film. The saturated fabric on the HDPE thin film was then placed on the shelf of a Usifroid (Model No—SMH1575, Serial No—16035) lyophilization unit at a temperature of approximately −50° C. The frozen, saturated fabric on the thin film (thickness less than 0.005 in) then underwent a full lyophilization cycle. A very flexible patch with trapped air bubbles and uneven distribution of Na—CMC through knitted CORC fabric was formed. In addition, defects were noted in the form of "lines", due to the instability of the thin film during lyophilization.

EXAMPLE 30

Hemostatic Performance of Wound Dressings in Porcine Splenic Incision Model

A porcine spleen incision model was used for hemostasis evaluation of wound dressings prepared according to Examples 27-29, using a standard hemostatic wound dressing as a standard. The materials were cut into 2.5 cm×1.5 cm rectangles. A linear incision of 1.5 cm with a depth of 0.3 cm was made with a surgical blade on a porcine spleen. After application of the test article, digital tamponade was applied to the incision for 2 minutes. The hemostasis was then evaluated. Additional applications of digital tamponade for 30 seconds each time were used until complete hemostasis was achieved. Approximately 100% of tested articles to achieve hemostasis within 3 minutes are considered to demonstrate good hemostatic efficacy. Table 6 lists the results of the evaluation.

TABLE 6

Hemostatic performance of dressings
Percent of test samples to achieve hemostasis within the time period

| Sample | 0–3 (min) | 4–7 (min) |
|---|---|---|
| Surgicel Nu-Knit ® | 0% | 100% |
| Example 27 | 100% | 100% |
| Example 28 | 0% | 100% |
| Example 29 | 0% | 100% |

As indicated from Table 6, hemostatic wound dressings prepared by the process of the present invention provide hemostasis faster, while those prepared by comparative processes fail to provide similarly rapid hemostasis.

EXAMPLE 31

Method of Analysis for Water-Soluble Oligosaccharides 150.0 mg of the conditioned fabric substrate to be analyzed is cut to a size approximately 0.5"×2" and placed into a test tube. The test tube is filled with approximately 30 ml of with distilled or deionized water and a stopper placed in the test tube. The tube then is stored at 70° C. for approximately 17-18 hours. The substrate sample is filtered through a glass crucible having a fritted disc of coarse or medium porosity. The filtrate containing the water-soluble oligosaccharide is transferred to pre-weighed aluminum dishes and evaporated to dryness. The residue is cooled in a desiccator containing phosphorous pentoxide and weighed. The water-soluble oligosaccharide content is calculated using the formula:

% Water-soluble oligosaccharide Content=[(Bf)/Wt]×100 where Bf is the weight of the water-soluble oligosaccharide (filtrate) and Wt is the total weight of the residue and filtrate.

We claim:

1. A process for making a wound dressing for use with moderate to severe bleeding, the wound dressing comprising a fabric substrate that comprises oxidized regenerated cellulose fibers and from about 8 to about to about 20 percent by weight of water-soluble oligosaccharides; and a biocompatible, water-soluble or water-swellable polymer matrix of sodium carboxymethyl cellulose, the process consisting of the steps of:
- providing a solution having dissolved therein sodium carboxymethyl cellulose,
- providing a fabric substrate having a first surface and a second surface opposing said first surface, said fabric substrate having flexibility, strength and porosity effective for use as a hemostat, said fabric substrate comprising a carboxylic-oxidized cellulose fibers and from about 8 to about 20 percent by weight of water-soluble oligosaccharides,
- contacting said solution with said fabric substrate under conditions effective to substantially homogeneously distribute said solution on said first and second surfaces and through said fabric substrate,
- lyophilizing said fabric substrate with said solution distributed there through, thereby forming a porous, polymeric matrix having a microporous structure.

2. The process of claim 1 wherein said fabric substrate comprises carboxylic-oxidized regenerated cellulose.

3. The process of claim 2 wherein said fabric substrate comprises from about 9 to about 12 percent by weight of said water-soluble oligosaccharides.

4. The process of claim 1 wherein the weight ratio of said sodium carboxymethyl cellulose to said fabric substrate is from about 1:99 to about 20:80.

5. The process of claim 2 wherein the weight ratio of said sodium carboxymethyl cellulose to said fabric substrate is from about 3:97 to about 10:90.

6. The process of claim 1 wherein said fabric substrate comprises from about 3 to about 20 percent by weight of water.

7. The wound dressing of claim 2 wherein said fabric substrate comprises from about 7 to about 13 percent by weight of water.

8. A hemostatic wound dressing made in accordance with the process of claim 1.

9. The wound dressing of claim 8 wherein said fabric substrate comprises carboxylic-oxidized regenerated cellulose.

10. The wound dressing of claim 9 wherein said fabric substrate comprises from about 9 to about 12 percent by weight of said water-soluble oligosaccharides.

11. The wound dressing of claim 8 wherein the weight ratio of said sodium carboxymethyl cellulose to said fabric substrate is from about 1:99 to about 20:80.

12. The wound dressing of claim 9 wherein the weight ratio of said sodium carboxymethyl cellulose to said fabric substrate is from about 3:97 to about 10:90.

13. The wound dressing of claim 8 wherein said fabric substrate comprises from about 3 to about 20 percent by weight of water.

14. The wound dressing of claim 9 wherein said fabric substrate comprises from about 7 to about 13 percent by weight of water.

\* \* \* \* \*